United States Patent
Lichter et al.

(10) Patent No.: US 10,501,792 B2
(45) Date of Patent: Dec. 10, 2019

(54) NANOCHANNEL COMPOSITIONS AND METHODS

(71) Applicants: Seth Harvey Lichter, Evanston, IL (US); Thomas Brian Sisan, Evanston, IL (US)

(72) Inventors: Seth Harvey Lichter, Evanston, IL (US); Thomas Brian Sisan, Evanston, IL (US)

( * ) Notice: Subject to any disclaimer, the term of this patent is extended or adjusted under 35 U.S.C. 154(b) by 0 days.

(21) Appl. No.: 15/110,546

(22) PCT Filed: Jan. 16, 2015

(86) PCT No.: PCT/US2015/011709
§ 371 (c)(1),
(2) Date: Jul. 8, 2016

(87) PCT Pub. No.: WO2015/109154
PCT Pub. Date: Jul. 23, 2015

(65) Prior Publication Data
US 2016/0355882 A1  Dec. 8, 2016

Related U.S. Application Data

(60) Provisional application No. 61/928,410, filed on Jan. 17, 2014.

(51) Int. Cl.
*C12Q 1/6869* (2018.01)
*G01F 1/00* (2006.01)
*G01N 33/68* (2006.01)
*B82Y 15/00* (2011.01)
*B82Y 40/00* (2011.01)

(52) U.S. Cl.
CPC .......... *C12Q 1/6869* (2013.01); *G01F 1/00* (2013.01); *G01N 33/6818* (2013.01); *B82Y 15/00* (2013.01); *B82Y 40/00* (2013.01); *Y10S 977/842* (2013.01); *Y10S 977/904* (2013.01)

(58) Field of Classification Search
CPC .... C12Q 1/6869; C01B 31/0253; B82Y 15/00
See application file for complete search history.

(56) References Cited

U.S. PATENT DOCUMENTS

| | | |
|---|---|---|
| 2008/0231361 A1 | 9/2008 | Ludwig |
| 2011/0168562 A1* | 7/2011 | Nuckolls .............. C12Q 1/6869 204/600 |
| 2011/0220191 A1 | 9/2011 | Flood |
| 2011/0253630 A1 | 10/2011 | Bakajin et al. |

OTHER PUBLICATIONS

Kuo et al, Unidirectional motion of a water nanodroplet subjected to a surface energy gradient, 2012, Physical Review E 85, 056301, pp. 1-7 (Year: 2012).*
Lu, Accelerating water transport through a charged SWCNT: a molecular dynamics simulation, 2013, Phys.Chem. Chem. Phys., 15, 14447-144457 (Year: 2013).*
PCT International Search Report for counterpart application PCT/US15/11709 (4 pages, dated Jun. 19, 2015).
PCT Recordation of Search History for counterpart application PCT/US15/11709 (3 pages, dated Mar. 27, 2015).
PCT Written Opinion of the ISA for counterpart application PCT/US15/11709 (19 pages, dated Jun. 19, 2015).
Xia et al. "Asymmetry of the water flux induced by the deformation of a nanotube" Chin. Phys. B vol. 21, No. 5 (2012) (054703 1-6) [cited in PCT International Search Report above].
Zhao et al. "Individual Water-Filled Single-Walled Carbon Nanotubes as Hydroelectric Power Converters" Advanced Materials, vol. 20 (2008) (1-5) [cited in PCT International Search Report above].
Excerpts of Sisan Dissertation "Single-file Transport through Carbon Nanotubes by Soliton Propagation" [portions provided by ISR, cited in PCT International Search Report above], embargoed until Mar. 4, 2014 and not publicly available any earlier than Jul. 25, 2014.
Full Sisan Dissertation "Single-file Transport through Carbon Nanotubes by Soliton Propagation" Part 1 of 2 (pp. 1-109), embargoed until Mar. 4, 2014 and not publicly available any earlier than Jul. 25, 2014.
Full Sisan Dissertation "Single-file Transport through Carbon Nanotubes by Soliton Propagation" Part 2 of 2 (pp. 110-242), embargoed until Mar. 4, 2014 and not publicly available any earlier than Jul. 25, 2014.
ProQuest e-mail dated Jun. 6, 2016 from Kristin Danko to Dr. Seth Lichter and Dr. Tom Sisan confirming publication embargo on Sisan Dissertation until Mar. 4, 2014.
Letter dated May 16, 2016 from Kurt Munson, Head, Access Services Northwestern University Library confirming Sisan Dissertation was not publicly available or discoverable until Jul. 25, 2014.

* cited by examiner

*Primary Examiner* — Narayan K Bhat
(74) *Attorney, Agent, or Firm* — Loeb & Loeb LLP

(57) ABSTRACT

Disclosed herein is a composition comprising a nanochannel and a contained substance, wherein the nanochannel comprises a single-file nanochannel and the contained substance comprises a plurality of substance particles arranged in a single-file chain within the nanochannel. Methods and systems for molecular transport of a substance through a nanochannel are also provided that rely upon the use of nanojumps, where nanojumps mediate the transport through the nanochannel.

94 Claims, 27 Drawing Sheets

(4,4)   (5,5)   (6,6)

NANOCHANNEL COMPOSITIONS AND METHODS

CROSS-REFERENCE TO RELATED APPLICATIONS

This international PCT Application claims the benefit of priority from U.S. Provisional Patent Application No. 61/928,410, filed Jan. 17, 2014, entitled, "NANOCHANNEL COMPOSITIONS AND METHODS", which is incorporated here by reference in its entirety.

FIELD OF THE INVENTION

The present disclosure relates to novel compositions comprising carbon-based and other materials as channels for controlling matter. In particular, a novel composition of matter comprising nanochannels and another substance or substances and methods for the precise control of matter within, through, and near nanochannels are disclosed.

BACKGROUND OF THE INVENTION

Controlling matter within nanochannels at atomic scale resolution is crucial for a wide variety of applications, including desalination devices and other types of chemical separations, deposition of quantum dots and molecule-by-molecule deposition, in general, of organic and inorganic molecules, fabrication of nanoscale devices at molecular resolution, precise DNA recording, precision movement of DNA and other biopolymers and other polymers, control of chemical reactions molecule-by-molecule, angstrom-scale movement of macroscale objects, and enabling new interactions between molecules within nanochannels and external particles or polarons, excitons or other types of quasi-particles. Flow through nanochannels is a crucial component of a wide variety of applications for which tunable transport properties are advantageous. For example, flow through nanochannels is a crucial component of a wide variety of applications for which a molecule from a solution is selectively transported with low energy input.

Nanoscale channels are not simply miniaturized microscale channels. However, in prior art methodologies, the transport is assumed continuous as in a pipe, and can not be discretely metered by the attributes of the nanochannel and transported molecules. In conventional methodologies, the substance being transported is treated as having a homogeneous density along the nanochannel.

In the conventional treatment of a single-file of molecules, the prediction in some cases is that there would be no transport, as predicted by the no-slip boundary condition. In other cases, in which a slip coefficient is introduced, the transport, at each instant in time, is constant at each cross section.

The delivery of large molecules by flow external to the nanotube has been numerically simulated (Patra and Král, J. Am Chem. Soc. 133: 6146 (2011), while the transport of charged molecules on the outside of nanotubes has been numerically simulated (Král and Wang, Chem. Rev. 113: 3372 (2013)).

Prior fabricated nanochannel devices have employed nanochannels with of a width where several of the atoms or molecules that enter the channels can fit within the cross section of the nanochannel. In contrast, reports of partially filled narrow nanochannels, for example (5, 3) carbon nanotubes, are relatively recent (Qin et al., Nano Lett. 11:5 (2011); Cambre et al., Phys. Rev. Lett. 104:20 (2010)).

While bulk water freezes near 0 degrees C. at standard pressure (1 atm), water within narrow carbon nanotubes is observed in numerical simulation in a solid-like state at higher temperatures (Wang et al., Science 322:5898 (2008)). The structure of contained frozen water is thought to depend on channel diameter. Wang et al. do not consider transport through nanochannels.

In prior art computer simulations, short single-file nanochannels are simulated being used for desalination (Corry, J Phys. Chem. B 112:5 (2008), Kalra, Garde and Hummer, Proc. Natl. Acad. Sci. USA 100: 10175 (2003)). In fluids applications, such as lab-on-a-chip devices, conventional methodologies suggest that channel lengths should be minimized to reduce power requirements. Additionally, in prior art channels wider than those for single-file flow are used for desalination. The use of wider channels is thought to always increase the volumetric flow rates of water. Molecular groups at the channel entryway hinder the entry of ions into the large channels (Majumder et al., J. Memb. Sci. 316:1-2 (2008)). There, wide channels are used to increase the volumetric flow rates of water. In prior art, nanochannels are modeled as pipes (Majumder et al., Nature 438:7064 (2005); Holt et al., Science 312:5776 (2006)).

In prior art, single-file substances within nanochannels are assumed to be essentially incompressible. In some prior simulations and theoretical models (Berezhkovsky and Hummer, Phys. Rev. Lett. 89:6 (2002); Zhu et al., Biophys. J. 85:1 (2003)), contained substances span the full length of single-file nanochannels and are treated as an incompressible rod. References are made to the collective motion of the particles and "collectivity", as is appropriate for rod-like motion. In other treatments (Chou, Phys. Rev. Lett. 80:1 (1998)), the atoms or molecules making up the contained substance occupy discrete sites within the nanochannel, or such sites may be unfilled. Thus, contained substances form contiguous incompressible segments spanning sequentially filled sites, which are separated from each other by any number of discrete contiguous vacancies. Contiguous segments are rod-like and the spacing between neighboring substance particles is uniform.

In conventional methodologies, it is considered to be desirable to decrease the roughness in order to increase flow. U.S. Pat. No. 7,341,651 B2 (2008) to Regan et al. proposed to use an electric field to move molecules along a carbon nanotube; however, the carbon nanotube of Regan et al. does not include precise and controllable step-like advance. Regan et al. state that the transport occurs "without the atoms (or clusters of atoms) being . . . stuck on the channel." For materials that are solid at the operating temperature, Regan et al. propose a means to heat the material, and state "it is necessary that the channel be sufficiently warm to permit atomic movement". Thus heating is considered advantageous. The device of Regan et al. is limited to charged molecular materials.

Ghosh et al., Science 299:1042 (2003) investigated the flow of water past a bundle of carbon nanotubes and speculated that there is a coupling between the induced voltage and the external classical Poiseuille flow. The generation of a voltage difference in a 1.6 nm carbon nanotube on application of a current in the presence of external water vapor was investigated by Zhao et al., Adv. Mat. 20:1772 (2008).

There is a need to more advantageously provide means to control, adjust, and tune the flux of water or other atoms, molecules, ions, electrons, or other types of particles, through nanochannels. Nanochannels may be used to transport substances while excluding other substances. The ability of nanochannels to allow passage of particular substances while excluding others, is the basis for a variety of applications. For example, water can be allowed passage while excluding sodium, chlorine and other ions, and so these types of nanochannels can be used for desalination.

SUMMARY OF THE INVENTION

In a first respect, a composition that includes a nanojack is provided. The nanojack includes a nanochannel and a contained substance. The nanochannel includes a single-file nanochannel and the contained substance comprises a plurality of molecules or a long molecule, such as a polymer—for example a protein or DNA strand or RNA strand—that is composed of monomers, arranged in a single-file chain within the nanochannel. In a first aspect, the nanochannel includes a nanochannel open at both ends. In one embodiment of this aspect, the nanochannel is selected from single-walled nanotubes, double-walled nanotubes, and multi-walled nanotubes. In another embodiment of this aspect, the nanochannel comprises a single-walled nanotube. In a refinement of this embodiment, wherein the single-walled nanotube is a single-walled, armchair nanotube or a single-walled, zigzag-type nanotube. In yet another embodiment of this aspect, the nanochannel includes a covalently bonded crystalline unit cell. In a refinement of this embodiment, the covalently bonded crystalline unit cell is selected from carbon, silicon carbide and boron nitride. In a second aspect the single-file nanochannel includes a peptidic nanochannel. In an embodiment of this second aspect, the peptidic nanochannel includes a helical winding of a polymeric peptide. In a third aspect, the substance is selected from aqueous mediums, organic mediums, and inorganic mediums. In foregoing embodiments, the nanojack includes a nanochannel having sufficient length to include a nanojump. In the foregoing embodiments, the nanojack further includes a nanojump or plurality of nanojumps. In one embodiment, an array of nanojacks is provided.

In a second respect, a composition that includes a nanojack is provided, wherein the nanojack includes a nanochannel and a contained substance. The nanochannel includes a single-file nanochannel having sufficient length to include a nanojump and the contained substance includes a plurality of molecules or a long molecule, such as a polymer—for example a protein or DNA or RNA—that is composed of monomers, arranged in a single-file chain within the nanochannel. In a first aspect, the nanochannel includes a nanochannel open at both ends. In one embodiment of this aspect, the nanochannel is selected from single-walled nanotubes, double-walled nanotubes, and multi-walled nanotubes. In another embodiment of this aspect, the nanochannel comprises a single-walled nanotube. In a refinement of this embodiment, wherein the single-walled nanotube is a single-walled, armchair nanotube or a single-walled, zigzag-type nanotube. In yet another embodiment of this aspect, the nanochannel includes a covalently bonded crystalline unit cell. In a refinement of this embodiment, the covalently bonded crystalline unit cell is selected from carbon, silicon carbide and boron nitride. In a second aspect the single-file nanochannel includes a peptidic nanochannel. In an embodiment of this second aspect, the peptidic nanochannel includes a helical winding of a polymeric peptide. In a third aspect, the substance is selected from aqueous mediums, organic mediums, and inorganic mediums. In the foregoing embodiments, the nanojack further includes a nanojump.

In a third respect, a composition that includes a nanojack is provided. The nanojack includes a nanochannel and a contained substance, wherein the nanochannel includes a single-file nanochannel having a nanojump. In a first aspect, the nanochannel includes an open-ended nanochannel. In one embodiment of this aspect, the nanochannel is selected from single-walled nanotubes, double-walled nanotubes, and multi-walled nanotubes. In another embodiment of this aspect, the nanochannel comprises a single-walled nanotube. In a refinement of this embodiment, wherein the single-walled nanotube is a single-walled, armchair nanotube or a single-walled, zigzag-type nanotube. In yet another embodiment of this aspect, the nanochannel includes a covalently bonded crystalline unit cell. In a refinement of this embodiment, the covalently bonded crystalline unit cell is selected from carbon, silicon carbide and boron nitride. In a second aspect the single-file nanochannel includes a peptidic nanochannel. In an embodiment of this second aspect, the peptidic nanochannel includes a helical winding of a polymeric peptide. In a third aspect, the substance is selected from aqueous mediums, organic mediums, and inorganic mediums.

In a fourth respect, the nanochannel may contain a substance and be closed at both ends. In a preferred embodiment, nanojumps can interact with externally imposed fields.

In a fifth respect, a method of molecular transport of a substance through a nanochannel is provided. The method includes the steps of providing a nanojack, and creating at least one nanojump within the nanojack. The nanojump or nanojumps effects molecular transport of the substance through the nanochannel. In this respect, the nanojack includes any of the compositions as provided in the first, second, third, and fourth respects. In a first aspect, the step of creating at least one nanojump within the nanojack includes applying a gradient condition to the nanojack. According to one embodiment of this aspect, the gradient is selected from pressure, temperature and electron motive force. In one embodiment the method includes moving molecules linearly within the nanochannel; in one embodiment the method includes moving molecules from within the nanochannel to a location outside of the nanochannel; in one embodiment the method includes moving molecules from outside of the nanochannel into a first end of the nanochannel, through the nanochannel, and out a second end of the nanochannel. In one embodiment molecules are moved from a first reservoir to a second reservoir; in one embodiment molecules are transported from a nanojack onto a substrate; in one embodiment molecules are transported from a nanojack into solution.

In a sixth respect, a system for molecular transport of a substance through a nanochannel is provided. The system includes a nanojack, a device; and a coupling. The coupling connects the nanochannel to the device. The device provides a condition to the nanochannel for effecting molecular transport of the substance through the nanochannel. In a first aspect, the coupling provides a connection to at least one of the following: (a) one end of the nanochannel, (b) both ends of the nanochannel, and (c) along a length of the nanochannel. In a second aspect, the condition generates or destroys nanojumps. In a third aspect, the molecular transport of a substance through a nanochannel deposits the substance on a surface or into a solution.

In a seventh respect, methods are provided for constructing a nanochannel molecular transport device, for modeling molecular transport, and for selecting operating conditions of the nanojack. Molecular modeling may be accomplished using the Frenkel-Kontorova (FK) model and Toda model. Construction of the nanojack includes material selection, nanojump number selection, and nanochannel size selection.

Selection of operating conditions of the nanojack may include selecting a number of nanojumps, the distance between nanojumps, and selecting the type and magnitude of potential difference across the nanojack.

In an eighth respect, compositions and methods are provided for nanojacks holding a substance static inside the nanochannel and where nanojumps are organized to control transmission of information. In one embodiment, a nanojack with one or more nanojumps is used to form or alter the index of refraction of a portion of a substance contained within the nanotube; in one embodiment, a nanojack with nanojumps is used as a memory device from which data can be recorded, stored, and retrieved.

In a ninth respect, methods and numerical techniques for usefully and expediently designing nanojacks and determining their operating conditions are disclosed.

DETAILED DESCRIPTION OF THE INVENTION

Figure 1:
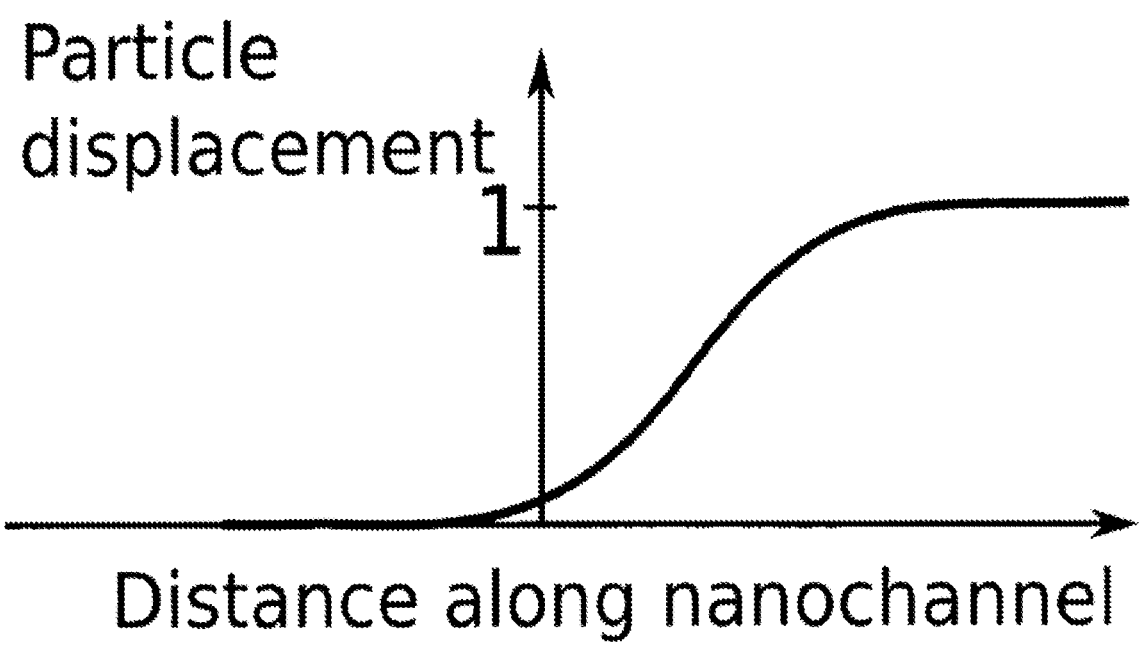
FIG. 1 is a schematic of displacement of particles versus distance along a nanochannel with one nanojump.

Compositions that contain substances within nanochannels, methods of transporting substances within nanochannels, and methods of designing and using nanojacks are presented in this disclosure. The disclosed materials and methods for particles, particle movement, and particle control within and near nanochannel-based devices provide for certain advantages in applications including condition-dependent, single-file movement of molecules having tunable transport properties.

Definitions

To aid in understanding the invention, several terms are defined below.

The terms "comprises", "includes", "having" and grammatical equivalents are open terms. For example, the term "includes" should be interpreted as "includes but not limited to". As a second example, the term "has" should be interpreted as "has at least". As a third example, the term "comprises" should be interpreted as "has at least".

The articles "a" and "an" refer to one or to more than one (for example, to at least one) of the grammatical object of the article.

The terms "about" and "approximately" shall generally mean an acceptable degree of error for the quantity measured given the nature or precision of the measurements. Exemplary degrees of error are within 25 percent (%), and typically, within 10% of a given value or range of values.

Furthermore, in those instances where a convention analogous to "at least one of A, B and C, etc." is used, in general such a construction is intended in the sense of one having ordinary skill in the art would understand the convention (for example, "a system having at least one of A, B and C" would include but not be limited to systems that have A alone, B alone, C alone, A and B together, A and C together, B and C together, and/or A, B, and C together). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or "B" or "A" and "B."

All language such as "from," "to," "up to," "at least," "greater than," "less than," and the like, include the number recited and refer to ranges which can subsequently be broken down into subranges.

A range includes each individual member. Thus, for example, a group having 1-3 members refers to groups having 1, 2, or 3 members. Similarly, a group having 6 members refers to groups having 1, 2, 3, 4, 5, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

An "inhomogeneous distribution" means non-uniform density along a nanochannel, as exemplified by measurement methods disclosed herein.

The substance that fills or otherwise is contained in the nanochannel can be comprised of atoms, molecules, colloids, or particles. The substance is referred to as being comprised of "molecules", "atoms", "particles", "material", "matter", "contained particles", "substance particles", or grammatical equivalents, each term does not exclude the other terms. Substance particles need not be identical, for example the substance may be composed of different types of substance particles. Substance particles and related terms can refer to the subunits of a longer molecular chain. For instance, if a polymer fills a nanochannel, the substance particles may be the individual atoms of the polymer chain or the monomers.

A "nanojack" refers to a novel composition of matter that includes the nanochannel together with a contained substance, wherein the contained substance having a chain of sufficient length as presented in the disclosure. By "chain" means a sequence of substance particles that are close enough together. By "close enough" means that the propagation of the nanojumps disclosed herein is possible. In some embodiments, the substance particles would be spaced at a distance from one another of 3 sigma or less, where sigma is the bulk spacing.

A "nanojump", sufficiently distant from other nanojumps, refers to a localized region within a contained substance where the contained substance particles are in relatively less periodic positions compared with periodic particle positions outside of the nanojump region. The location of a nanojump can be identified as the point of maximal misalignment. A nanojump may be verified by measurement methods described herein. When subject to a large enough force per particle, the magnitude of the velocity of the particles within the nanojump is larger than that of a region of similar size outside of the nanojump.

The terms "nanochannel" and "nanotube" interchangeably refer to a channel or tube having a diameter, also referred to herein as the "internal diameter", from about 0.25 nm to about 100 nm. For a single-walled carbon nanotube, the diameter is measured between radii of the centers of the atoms in the nanochannel wall across the diameter, or the nearest approximation. For a multi-walled carbon nanotube, the measurement refers to the innermost wall. For other types of nanotubes, the measurement refers to the innermost wall or collection of atoms that are in closest proximity to the substance molecules. For channels whose cross sections are not circular or approximately circular an average or effective diameter would be used. The "nanochannel" or "nanotube" is also referred to as the "substrate". The term "nanotube" is not restricted to "carbon nanotube", "boron-nitride nanotube", or "silicon-carbide nanotube".

By CNT, BNNT, or SiCNT is meant carbon nanotube, boron-nitride nanotube, or silicon-carbide nanotube, respectively.

The statistical nature of molecular-scale events necessitates the use of qualifiers such as "in large measure" or "nearly always." For example, substance particle positions may fluctuate due to thermal energy. These and similar qualifiers are implied elsewhere herein as appropriate when referring to stochastic phenomena or molecular scale events.

"Single-file nanojack", or "single-file nanochannel", or grammatical equivalents, refer to a nanojack such that the contained substance is single-file. Single-file nanochannels for substance A can be different from single-file nanochannels for substance B. By "single-file" or grammatical equivalent is meant that the sequence of substance particles along the nanochannel remains in large measure or absolutely unaltered. Consequently, if a particle identified as I is just ahead of particle J, then particle I remains nearly always in advance of particle J. In general, one substance particle cannot pass the substance particle in front of it, nor can it be passed by another substance particle. When the substance is a polymer, such as a protein or DNA, or some other long-chain molecule, then single-file means that monomers of the polymer remain nearly always ordered within the nanochannel, such that if a monomer I is just ahead of monomer J, then monomer I remains nearly always in advance of monomer J. In general, one monomer cannot pass the monomer in front of it, nor can it be passed by another monomer. The nature of single-file for a long molecule such as a polymer should also be clear from the definition given of the substance particles.

By the "Frenkel-Kontorova model", "FK model", "Frenkel-Kontorova equations", "FK equations", or grammatical equivalents, is meant any of the discrete forms and other relevant approximations, such as continuum approximations of the FK model, for example, the sine-Gordon model. The "Toda model", or grammatical equivalents, may also refer to the Toda lattice. Reference to any of these models or equations may also refer to models that comprise elements of both FK and Toda types of models.

"A" and "A" topped by a ring, are used as an abbreviation for angstrom. "fs" is used as an abbreviation for femtosecond. In general, standard SI abbreviations are used.

Examples identified herein are either based solely on modeling or are meant to be illustrative and prophetic only.

Other terms and expressions are defined elsewhere herein.

The theory, explanations and results of the provisional application are hereby expressly incorporated in their entirety.

Nanojacks, methods of designing nanojacks, and systems employing nanojacks are presented in this disclosure. Nanojacks, designed by the described methods, provide for certain advantages over prior designed nanochannels and provide for a new modality of atomic-scale control. Nanojacks, and nanojack devices, and nanojack systems designed according to the methods herein, lead to a more efficient, effective, and/or better-controlled transport, which can, among other advantages, be more economically competitive, work better, produce new capabilities, or work with less energy input. The novel properties and capabilities arise in many instances, from the number of, type of, and length of nanojumps within nanojacks.

Nanojumps have properties described by the mathematical theory of topological solitons or dynamical solitons. In some cases we use the Frenkel-Kontorova (FK) equation, or substantially similar equation, to model nanojumps. In other cases, where the interaction between substance particles is significantly nonlinear, nanojumps can be modeled as solitons of the Toda lattice or as hybrid FK-Toda solitons.

Nanojacks have novel properties including that the substance can be transported at temperatures well below the bulk freezing temperature of the substance, the substance can be aliquoted in discrete molecular amounts, if a long molecule, it can be moved in discrete molecular increments, in some cases, flow rates may depend upon the nonlinearity of the molecular interactions of the substance, and in some cases flow rates depend upon the molecular roughness of the nanotube.

Some of the properties and behaviors of nanojacks are contrary to current thinking about flow in nanochannels and contrary to the manner in which current devices are thought about and designed, including that the flow can occur below the bulk freezing temperature of the substance and that the molecular roughness is an ingredient contributing to, rather than impeding, flow.

The conventional view of nanochannels with a contained substance, except when gaseous, is that the contained substance is viewed as incompressible, and is thought to move within the nanochannel approximately as a collective incompressible assembly, with approximately uniform spacing between substance particles.

In contrast, in some of the compositions disclosed herein, the spacing between substance particles within nanochannels is made to be modulated in a particular manner by the potential arising from the atoms composing the nanochannel wall, the external conditions, and inter-particle interactions. The spacing between substance particles is modulated such that in many cases, the particles can be assigned to two types of regions. This assignment is motivated by the theory and numerical methods presented herein. In the illustrative situation described here, there is only one nanojump present in a long nanochannel. Some substance particles are relatively aligned with the potential in the sense that these substance particles reside positioned relatively equally spaced and near locations of minima of the potential. Methods for calculating this potential energy are disclosed herein. In general, these particles reside on either side of the nanojump. The other substance particles are in relative misalignment with the potential in the sense that they are not equally spaced and that they are located relatively further away from the closest potential energy minimum. Such regions of misalignment are a key type of nanojump. It is to be understood that a particular particle within a nanojump can be instantaneously closer to a minima than a particular particle outside of the nanojump. Nonetheless, it is possible to designate a region within which the particles within that region are, taken together, in relative misalignment compared with the particles outside of that region.

Another description of the spacing of substance particles within nanojacks, in the case of a single nanojump within a long nanochannel, is as follows. As the molecules of a contained substance travel along the nanochannel, they experience variations in potential energy. As disclosed herein, a periodic potential of a nanochannel is determined from which a wavelength and amplitude is derived. A Fourier analysis of this experienced potential yields one type of measurement of the wavelength and amplitude of the interior potential. One of the Fourier components may be significantly larger than other components. The wavelength of this component alone, in many cases, can be used as the interior potential wavelength. In a simple embodiment, the periodic potential can be sinusoidal. Each particle of the contained substance is assigned zero displacement relative to a minima of that potential, such that if each particle were to be placed at its assigned minima, its displacement would be zero, and the zeros of each particle serves as the origins from which their displacements are measured. An example of particle positions within a nanojack with one nanojump is shown in FIG. 1. However, the figure is drawn as if there were so great a number of particles that the points representing the individual particles could not be individually distinguished. The figure is also drawn for a case at low temperature, where thermal fluctuations are minimized. For the leftmost interval, the displacements are near zero. For the right-most interval, the displacements are near one. The units used to designate particle displacement, generally referred to as $u\_i$ are a characteristic periodicity of the potential. In general, the unit of displacement over one nanojump is the distance between minima or an integral multiple of this distance. The interval separating the left and right intervals is the interval of the nanojump.

Within nanojump regions, substance particles can be spaced more closely or less closely than outside of nanojumps, and are termed compression nanojumps and expansion nanojumps respectively, or grammatical equivalents.

Figure 2:
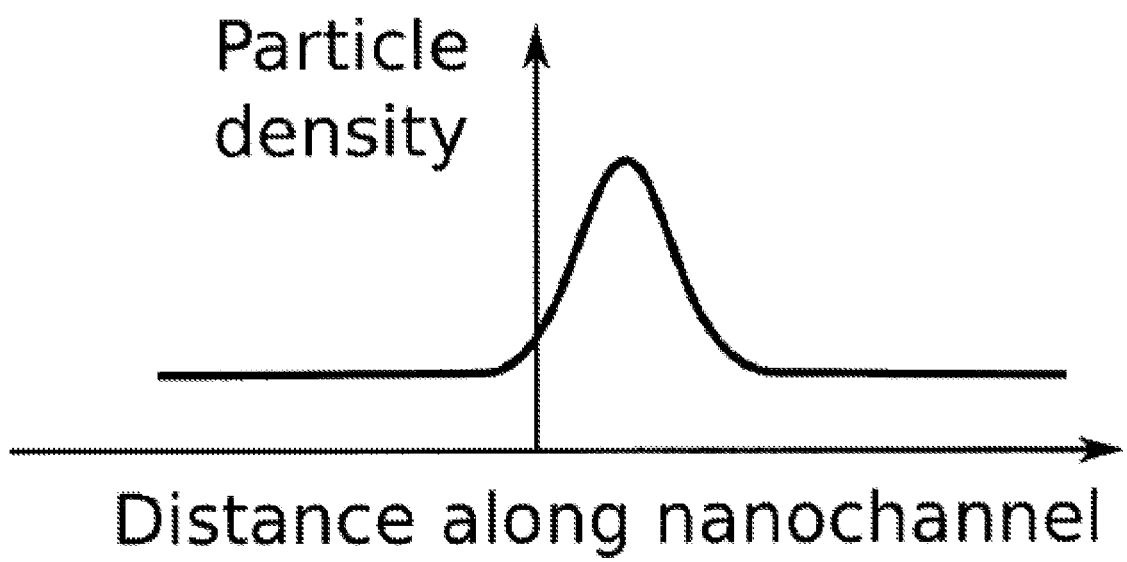
FIG. 2 is a schematic of density of particles versus distance along a nanochannel with one nanojump.

Another description of the spacing of substance particles of the composition disclosed herein, in the case of a single nanojump within a long nanochannel, is as follows. For purposes of this description, let there be a long nanochannel containing many substance particles. Now choose a length that is small compared with the length of the nanochannel but large compared with the spacing of the substance particles. Slide this window along the length of the nanochannel and measure the density of particles within the interval. As the window is slid along, it will sample the particles along the length of the nanochannel. Plot the density within the window versus its position. The interval in which the density departs from its nearly constant value is the interval of the nanojump. Different averaging windows can produce slightly different values of the width of the nanojumps. For the purpose of showing that nanojumps are present, the precise value of the width need not be important. A characteristic is that the density within a region differs from the density on either side of that interval. The example shown in FIG. 2 shows two nanojumps in which the density is higher than in the regions outside of the nanojump, in other words, a compression nanojump.

Figure 26:
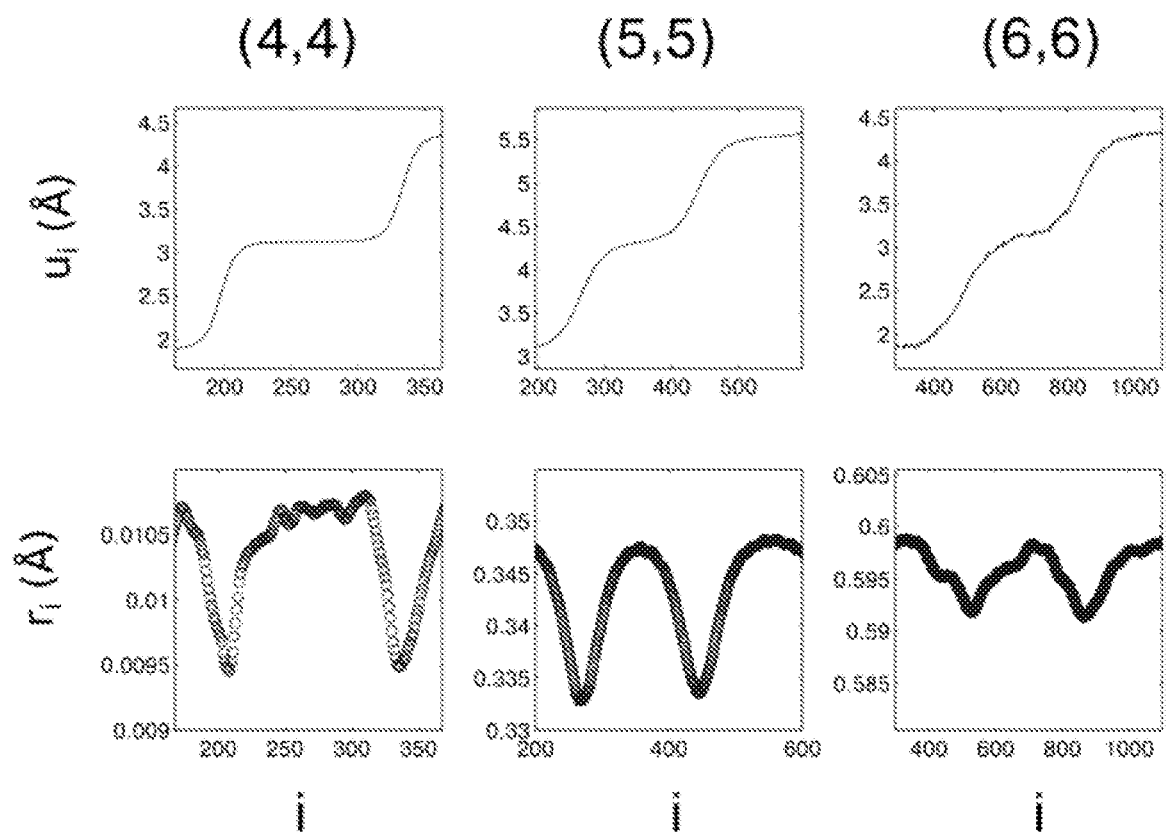
FIG. 26 shows that nanojumps in armchair CNTs may be accompanied by a perturbation in the radial positions of water molecules.

We also plotted the radial position $r\_i$ of the oxygen atoms versus the water index i in the lower set of panels in FIG. 26. The upper set of panels show the axial displacement, as seen in other figures. Each pair of upper and lower panels for, left to right, the (4,4), (5,5) and (6,6) nanotube, share a common abscissa and shows two nanojumps. For each nanotube, the water molecules in the nanojump also deviate in their radial position. Where axial density is high, axial pressure is also expected to be high, and the water molecules residing off the nanotube axis are pushed further off axis. In the region of expansion nanojumps, internal pressure is relieved and wall atoms are able to push water molecules in the nanojump region toward the center of the nanochannel. In other words with more space available, water molecules in the region of the nanojump relax toward the center of the channel. This type of radial perturbation has not been previously described, and is a consideration in our design methods.

Figure 3:
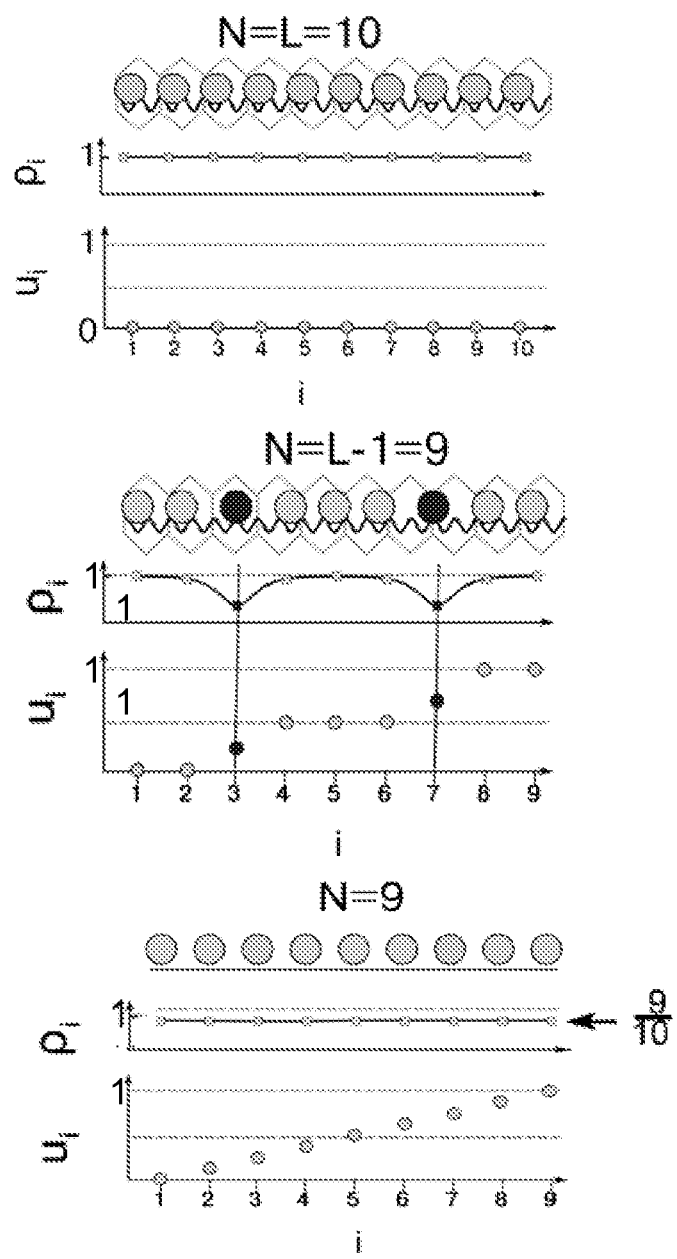
FIG. 3 is a schematic illustrating nanojumps in CNTs.

A more detailed illustration of both variables $u\_i$ and density is shown in FIG. 3, using water within CNTs near S=0. For water and similar size molecules in armchair CNTs, S is equal to number of atoms or molecules in the nanochannel minus the number of hexagonal rings along a line parallel to the CNT axis. In general, the definition of S needs to be suited to the particular nanojack. S=0 needs to correspond to a state with approximately uniform spacing between substance particles so that no nanojumps are present. In these drawings the variable $u\_i$ is normalized by the average spacing between the substance particles in the S=0 case, in this case two substrate wavelengths, or one CNT ring. In the leftmost panels S=0 as there is one substance particle for every two substrate wavelengths. The density, shown as the Greek letter rho on the figure, is constant along the channel and all $u\_i$=0. In the middle panels, one substance particle has been removed so that S=−1. Two expansion nanojumps are formed to compensate for the space of the missing substance particle. The density, rho, decreases in the region of the nanojumps. The variable $u\_i$ increases by ½ when moving across the nanojump, as particles on the right of the nanojump are displaced to the right relative to where they would be if the nanojumps were not present by half a carbon ring. In the right panels the substance particles are placed in a smooth channel, or one where the substrate potential amplitude is approximately zero. Though there are the same number of substance particles as in the middle panel, no nanojumps are formed and the density, rho, is constant along the channel. The displacement, $u\_i$, increases steadily from zero to 1.

Figure 4:
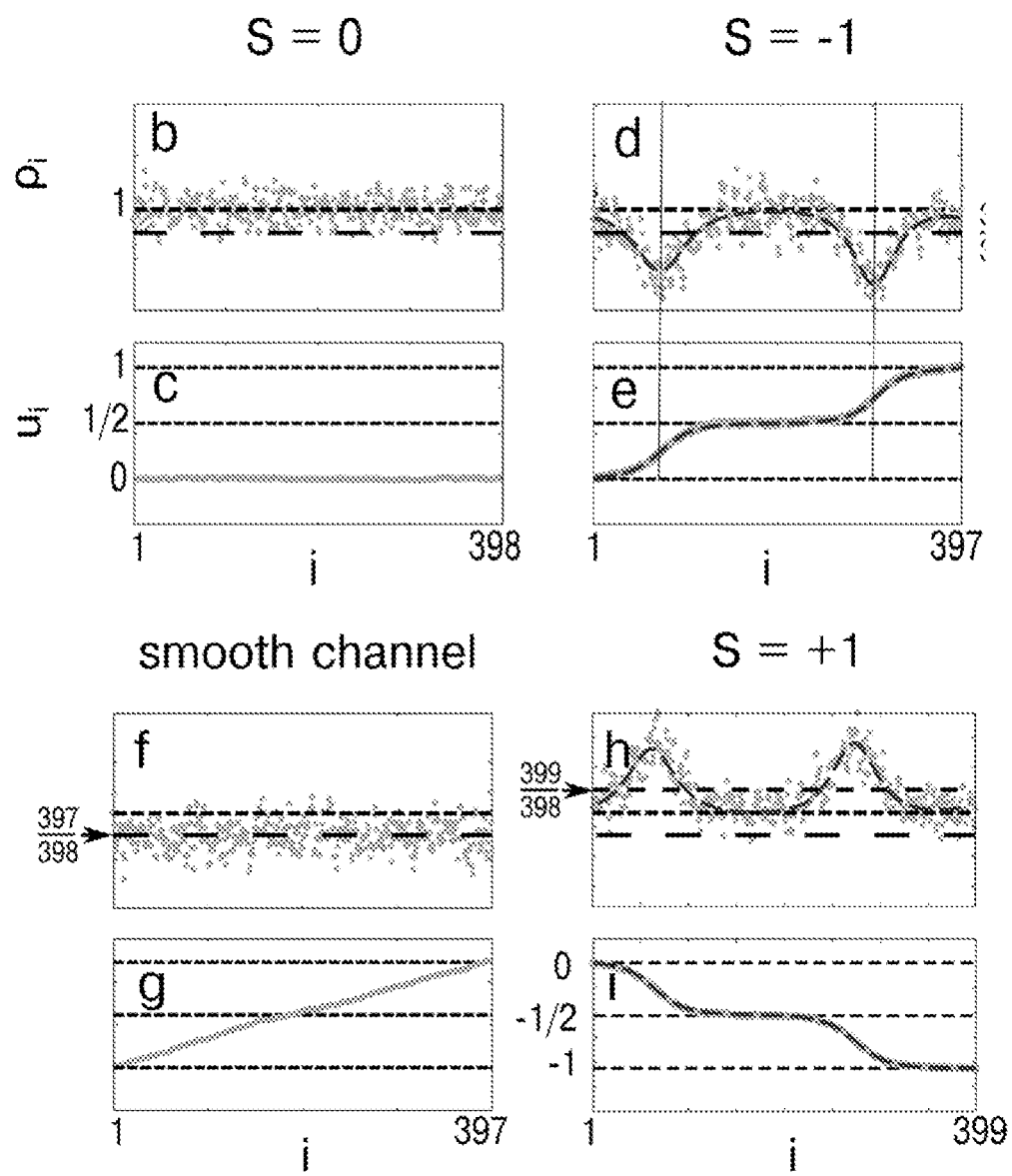
FIG. 4 shows numerical simulation examples of nanojumps in a nanojack comprised of water and a (5,5) carbon nanotube with 398 carbon rings along its length at 1 K.

FIG. 4 shows numerical-simulation examples of nanojumps in a nanojack comprised of water and a (5,5) carbon nanotube with 398 carbon rings along its length at 1 K. For the formula S=L-N, here L=398. In (b), (d), (f), and (h), each dot corresponds to a water molecule i=1, . . . , N. The local density $rho\_i$ centered at each water molecules is plotted. Panels (c), (e), (g), and (i) plot the displacement $u\_i$ of each water molecule. Each of the N $u\_i$, for I=1, . . . , N, has its own origin. The displacement $u\_i$ is measured relative to every other potential energy minima at the radial position of the water molecules, so that when a water molecule is located at the position of its reference minima, $u\_i$=0. This manner of referencing each of the N displacements to its own minima is different from the usual manner in which the displacement of all N molecules is measured relative to a single origin. Shown in (b) and (c) is the case for N=L=398, so S=0. When the number of water molecules is equal to the number of carbon rings, then each water is near its respective minimum, and displacement $u\_i$ is zero and density $rho\_i$ is nearly constant. Shown in (d) and (e) is the case for N=L−1=397, so S=−1, that is, there is one fewer water molecules than carbon rings. The water molecules do not distribute evenly along the length of the nanotube. Rather, two nanojumps are formed, seen as regions of lower density in (d) and regions in which the displacement, otherwise constant, varies. Shown in (h) and (i) is the case for N=L+1=399, so S=+1, that is, there is one water molecule more than the number of carbon rings. Water molecules do not distribute evenly along the length of the nanotube. Rather, two nanojumps are formed, seen as regions of higher density in (h) and regions in which the displacement, otherwise constant, varies. We disclose herein novel methods for predicting, describing, and designing the performance of nanojacks. As part of those methods, we introduce the use of soliton theory. Among other characteristics, the density and displacements observed in nanojumps can be described in part using the mathematical theory of solitons. Computations using soliton theory predict a hyperbolic secant form for the density variation, shown on (d) and (h) with a dashed line, which closely matches the nanojumps. Computations using solitons theory also predict an arctan form for the displacement, shown on (e) and (i) with a dashed line, which closely matches the nanojumps. For (f) and (g), unlike the other panels, the interaction of the nanotube with the water molecules was smoothed such that there was no or very small variation in potential in the axial or circumferential directions. For this case, S=−1. No nanojumps form, and the density is nearly constant, and the displacement increases linearly. This figure shows that, unlike in the conventional view of nanochannels, the relationship of the nanotube structure, here given by the number of carbon rings, and the water arrangement, here given by the number of water molecules, is a critical parameter in determining the formation of nanojumps.

Means to determine the width of the interval of the nanojump are given by Frenkel-Kontorova (FK) model theory, the theory of Toda models, or can be obtained through computer simulations. However, for the purpose of showing that nanojumps are present, the precise value of the width need not be important. A preferred characteristic is that the displacements change by one, in characteristic units, from one side of the nanojump to the other.

In other embodiments, the potential arises in large part from an externally applied field. In these cases, it is primarily this potential rather than the potential from the nanochannel walls alone that leads to nanojump formation.

In other embodiments, the nonlinearity of the force exerted between substance particles leads to nanojump formation. In these cases the Toda lattice is used to model nanojumps.

In other embodiments the nonlinearity of the interparticle interaction is significant and a nonlinear model such as the Toda potential is used in the FK model. Then a hybrid Toda-FK model results, where nanojump velocity depends on the nonlinearity.

The application of external excitations can create a nanojump comprised of a compression nanojump and expansion nanojump formed into a composite structure. The external excitation, which may, for example, be an optical, thermal or mechanical excitation, can sustain the composite structure, which without such excitation would be transient. In cases where both compression and expansion nanojumps are present within a nanochannel, a compression nanojump and expansion nanojump can combine into such a composite nanojump. Conversely, such a composite nanojump can break apart into an individual compression and expansion nanojump.

Nanojumps of a same type repel each other. In other words, two neighboring compression nanojumps within a nanochannel will exert a repulsive force on each other. Nanojumps of opposite type attract. In other words a compression nanojump will exert an attractive force on a neighboring expansion nanojump, and vice versa. An estimate for the size of the forces can be obtained by the theory of the FK model, as is known to those skilled in the art. When enough nanojumps of the same type occupy a channel a regular series of nanojumps can be formed, where a sequence of nanojumps line the channel at approximately even spacing. The nanojumps have different optical properties than outside of the nanojumps, in particular a locally different index of refraction. The equally-spaced nanojumps can be used to interact with light as a novel means to yield slow light, produce interference patterns, or other useful optical manipulations. The ability to change the spacing between the nanojumps by adjusting the operating conditions allows the nanojack to be tuned, which is an advantage in many applications.

The number of nanojumps within nanojacks depends in many cases on the number of contained particles residing within the nanochannel and the number of potential energy minima along the nanochannel. In one example the atoms of the nanochannel produce a potential such that the particles of the contained substance experience a sinusoidal or approximately sinusoidal potential energy. If there is one substance particle for every potential energy minima, then the substance particles can be located, evenly spaced, in every minima Consequently, there would be no nanojump (S=0). If external conditions were changed, such as by increase of the external pressure, an additional substance particle can enter the nanochannel. Consequently, substance particles can no longer fit evenly spaced in every potential minima and a compression nanojump can thereby be formed (S=+1). In a preferred embodiment the nanojack contains one nanojump; in a preferred embodiment the nanojack contains two nanojumps; in a preferred embodiment the nanojack contains two or more nanojumps; in a preferred embodiment the nanojack contains 10 or more nanojumps; in a preferred embodiment the nanojack contains 100 or more nanojumps; in a preferred embodiment the nanojack contains 1,000 or more nanojumps; in a preferred embodiment the nanojack contains 10,000 or more nanojumps; in a preferred embodiment the nanojack contains 100,000 or more nanojumps; in a preferred embodiment the nanojack contains 1,000,000 or more nanojumps; in a preferred embodiment the nanojack contains 1,000,000,000 or more nanojumps.

A similar description applies when there is one substance particle for every two of the substrate minima. There, substance particles will reside in every other potential minima, and similarly no nanojumps are present. However, two nanojumps are formed or destroyed for every change in the number of substance particles. In general, whenever there is one substance particle for every $n\_s$ substrate potential minima, where $n\_s$ is a positive integer, then no nanojumps are preferred, and $n\_s$ nanojumps are formed or destroyed for each change in the number of substance particles.

The geometric arrangement of potential minima within nanochannels is in some cases set by covalent bond lengths of atoms in the nanochannel wall and its crystal structure. In CNTs and similar nanochannels, the chiral indices (m,n) describe the crystalline unit cell. The values of m and n can affect the geometric arrangement of the minima of the potential.

In the conventional design of a tube for transport, properties of the tube to maximize transport can be specified independently of the properties of the substance. For example, for rapid flow it is conventionally seen as best to have a nanochannel that is as smooth as possible. In contrast, in the present disclosure, the performance of nanojack compositions depends on in many embodiments on the relationship of nanochannel properties with properties of the contained substance, and in some embodiments on the nonlinearity of the force between substance particles. As apparent to those suitably skilled in the art and as described herein, the wavelength of the potential relative to the spacing of the particles of the contained substance, or mismatch, is a preferred parameter in the performance of nanojacks. The strength of the interparticle interactions relative to the energy of the potential variations is a preferred parameter. When substance particle interactions are significantly nonlinear and can be made more or less nonlinear through external pressure, the strength of the nonlinearity may be a preferred parameter.

In contrast to conventional methodologies, in the present disclosure, the design of nanojacks depends on both the nanochannel and the contained substance. As apparent to those suitably skilled in the art and as described herein, the relative spacing of the nanochannel relative to the contained substance, or mismatch, is a parameter in the design of nanojacks. In a preferred embodiment, the rate of transport can be enhanced by properly matching the periodicity of the nanochannel potential against the spacing of the substance molecules.

A first key property of nanojumps is that the mobility of contained particles within nanojumps can be higher than in regions of alignment. Consequently, nanojumps can serve as the basis for transport within nanochannels. They can provide the mobility or contribute substantially to the mobility. In general, the presence of greater or lesser numbers of nanojumps can serve as greater or lesser numbers of transporters for transport.

A second key property of nanojumps is that nanojumps are localized, such that nanojumps meter discrete quantities of contained substance with passage of each individual nanojump. This flow discreteness can serve as the basis for applications such as the metering of individual atoms from the end of a nanochannel at a specific controllable rate.

Other advantageous properties of nanojumps are also disclosed as additional embodiments. For one exemplary embodiment, static nanojumps can be used in or serve as the basis for some nanotechnologies. For another exemplary embodiment, as substance particle spacing within expansion nanojumps is greater than outside of such nanojumps, such increases in substance particle spacing can serve as the basis for an electrical switch, where current flows freely in the absence of a nanojump, but current is impeded when encountering an expansion nanojump.

Figure 7:
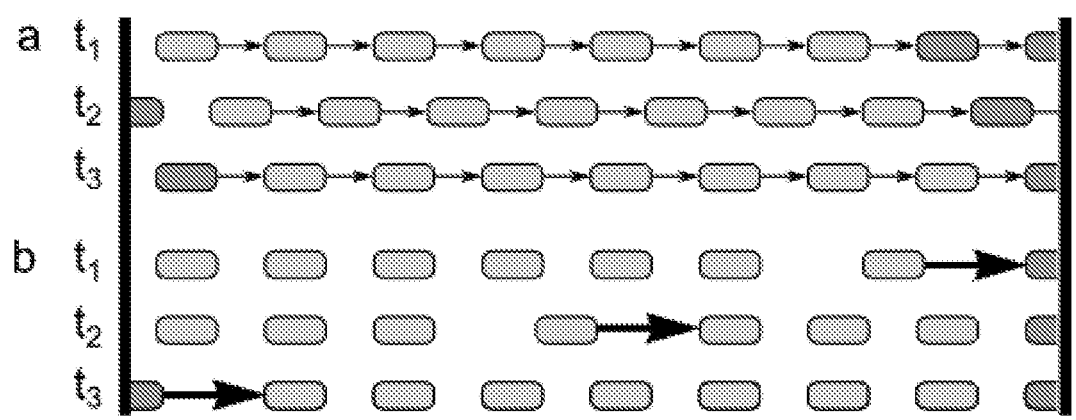
FIG. 7 illustrates contrasting views of nanochannel transport, shown at three different points in time t1, t2 and t3. Part (a) of the figure shows the conventional view: all molecules move together (aside from thermal motions). In contrast, part (b) illustrates transport by nanojump propagation according to the embodiments of the invention. In this illustration nanojumps are widely separated. Most contained molecules are nearly motionless, but, as illustrated here, near a region of low density, molecules shift positions. The average velocity is the same in parts (a) and (b). Arrow length is proportional to velocity. Only a short portion of the channel is represented.

One having ordinary skill in the art might not readily appreciate how nanojumps facilitate transport or how nanojumps can be used for discrete transport owing to the novel, non-obviousness of the present disclosure. To aid one having ordinary skill in the art with this appreciation, an analogy is made to a traffic jam, where gaps in traffic aid traffic flow, but the analogy should only serve as an introductory conceptual aid. As a car moves forward into a small gap, the gap propagates backwards, allowing the following car to move forward, and so on, as shown in FIG. 7. Cars within the region of the gap are much more mobile than cars away from the gap. As the gap passes, cars are incremented forward by equal amounts. An increase in the number of gaps will increase the net transport rate, and eventually neighboring gaps blend together. In an analogous manner, the passage of nanojumps increments molecules along the nanochannel and facilitates transport with fine control.

In many cases transport of a substance can be effected by applying a forcing across the nanochannel, such as, but not limited to, a hydrostatic pressure gradient, where, for example, a preferred time-varying or constant magnitude of applied pressure gradient can be determined from a computer simulation.

Another method to drive flow is by using the coupling between the substance and electron flow through nanochannels. For example, for water-filled CNTs, by setting up an electrical current through the nanotube, the electrons couple to the water molecules. Though not limited by theory, it is appreciated by those in the art that the flow of the electrons induces a force on the water molecules along the nanotube, resulting in a flow of water through the nanotube. Many substances are polarizable or otherwise interact with flowing electrons in the surrounding walls such as through phonon-electron coupling, consequently, such means are not limited to water. Other methods of effecting transport are also possible, such as by sound, light, electric, or magnetic field. It should also be appreciated that as a substance is advanced through a nanotube, an electric potential may be induced in the nanotube wall and this potential may be measured to determine flow amount, rate, and other properties of the contained substance Induced electric potentials may also serve as the basis of a novel means of flow-induced power generation.

Nanojack properties can be subject to new types of external controls, such as absolute pressure rather than simply pressure gradient. For example, by increasing the absolute pressure, average contained particle density can be increased, and thus a nanojack can be transformed, for example, from a nanojack with no nanojumps, into a nanojack with several nanojumps. Employing such a transformation, a nanojack can serve as a flow switch. Additionally, by the methods of nanojack design disclosed herein, the number of, type of, and length of nanojumps can be advantageously selected.

Methods and apparatuses are described to control flow through nanochannels. In one embodiment, there is a means to set the pressure difference and also the absolute pressures upstream and downstream of the nanochannels. The choice of pressures can be based on the results of numerical simulation or numerical calculation, where the numerical simulation models flow through nanochannels or the numerical calculation uses a model of such a system, or such values are pretabulated. From these results the absolute pressure can be chosen to achieve a spacing of substance molecules such that the transport has the desired properties.

Figure 6:
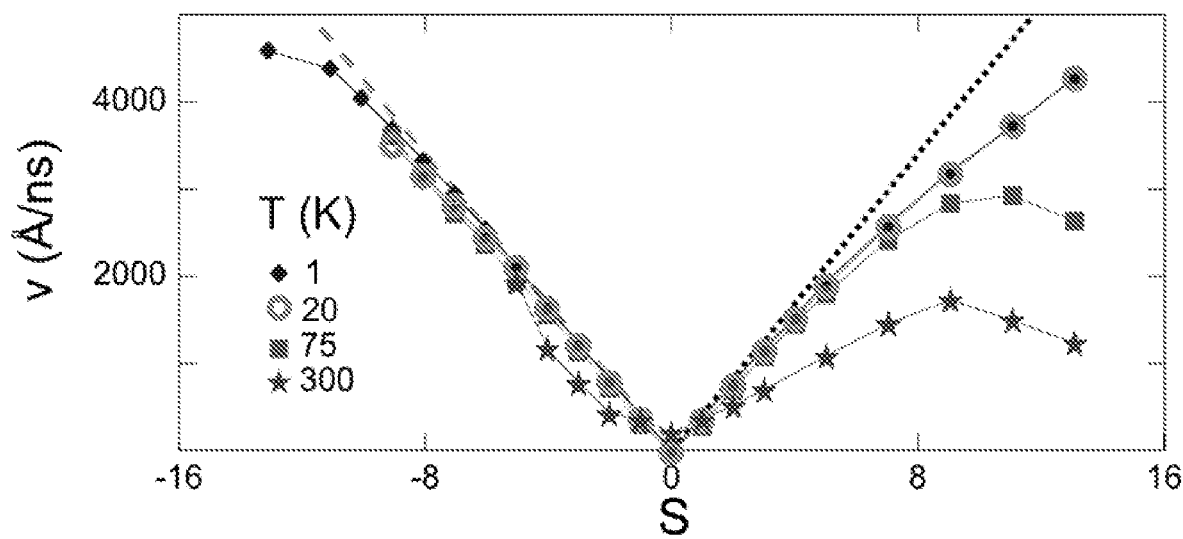
FIG. 6 shows flow rates v in angstroms per nanosecond as a function of the control parameter S, which is related to absolute pressure. Data is shown for four temperatures T, given in the label in kelvin.
Figure 23:
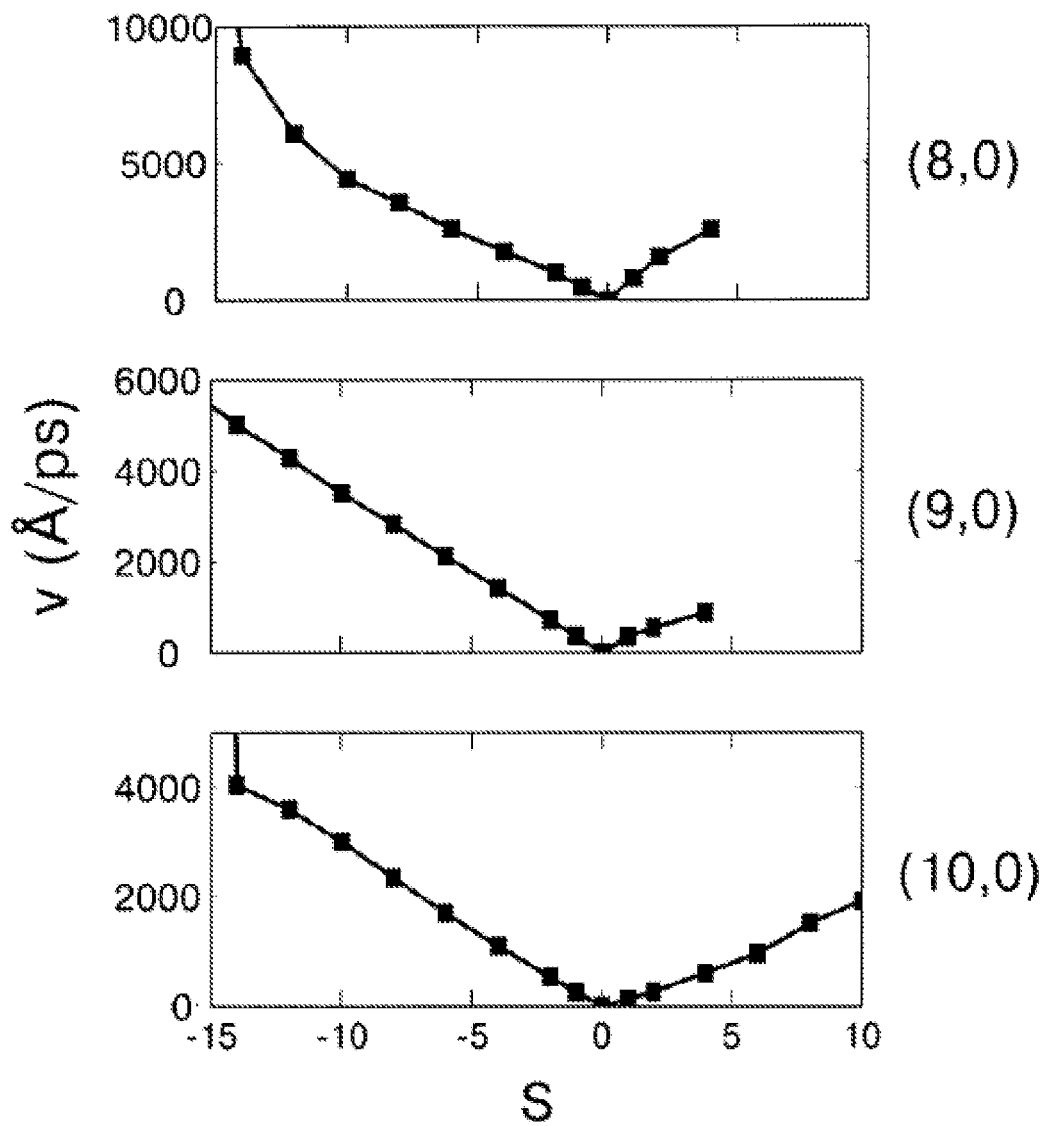
FIG. 23 shows flowrates of water in zigzag CNTs as a function of S.

When continuous flow is preferred, a high density of nanojumps is preferred. This is achieved, for example, through greater mismatch between the number of contained substance particles within the nanochannel and the number of potential energy minima. As external pressures affect the densities of contained particles within nanojacks, in some cases increasing the absolute pressure on both sides of a nanojack increases transport. This runs counter to conventional wisdom for economical and efficient transport through nanochannels. FIG. 6 shows flow rates of water in the (5,5) CNT as a function of the control parameter S, which is related to absolute pressure. For water and similar size molecules in armchair CNTs, S is equal to number of atoms or molecules in the nanochannel minus the number of hexagonal rings along a line parallel to the CNT axis. In general, the definition of S needs to be suited to the particular nanojack. S=0 needs to correspond to a state with approximately uniform spacing between substance particles so that no nanojumps are present. As S approaches 0 the number of nanojumps approaches zero and flowrate approaches zero. As S is proportional to the number of nanojumps, and each nanojump contributes equally to flow, the flowrate is linearly proportional to S near S=0. Farther from S nanojumps may interact with each other, or the parameters of the FK model—h, k, and lambda—may change, causing nonlinear changes in flowrate with S. Similar definitions are applicable to other types of nanochannels. For example, zig-zag carbon nanotubes are distinguished by n=0 in the pair of indices (m,n), and the interior wavelength is approximately 2.13 angstroms. In zig-zag carbon nanotubes, S corresponds to the number of nanojumps, whereas in armchair carbon nanotubes, 2S is equal to the number of nanojumps. Despite the difference in structure between armchair and zig-zag carbon nanotubes, the behavior of flow rate in zig-zag nanotubes versus S possesses features seen in CNTs composed of armchair carbon nanotubes, in particular, no flow at S=0, linear increase in flow speed as S increases from S=0, and linear increase in flow speed as S decreases from S=0, as shown in FIG. 23, for results from, from left to right, the (8,0), (9,0), and (10,0) zig-zag carbon nanotubes. This data is from simulations at 75 K, with applied force on each particle of 4, 2, and 1 pN, from left to right.

Figure 27:
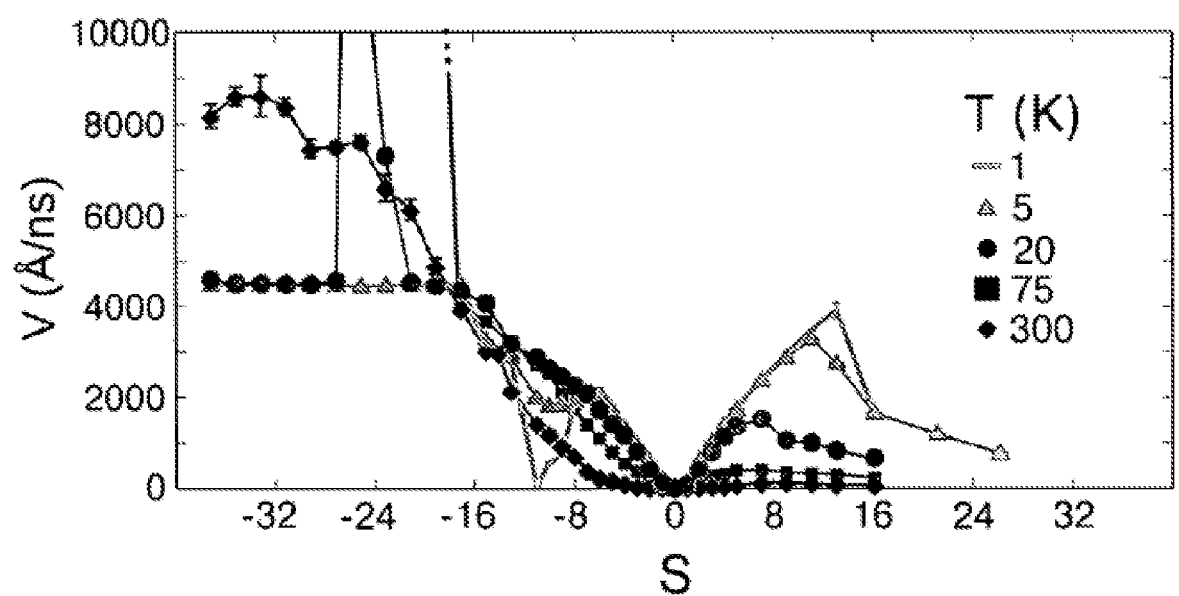
FIG. 27 shows flowrates in the (5,5) CNT at a range of temperatures at a larger range of S than in FIG. 6.

Since flow in nanochannels is a three dimensional problem in contrast with the FK model, which is one-dimensional, novel features arise. Since substance particles can lie along a variety of three-dimensional paths through the channel, the particles may sometimes experience the S=0 state along a dimension other than the channel axis. In FIG. 27, flowrates went to zero at low temperatures at an axial value of S=−11. Further investigation showed that S=0 along a circumferential direction.

In prior devices and descriptions, the flow rate through nanochannels is controlled only by a difference of pressure. This means of control is based on the view that flow in nanochannels occurs by the same process as flow occurs in a pipe. It is well known that the flow of incompressible liquids through large-diameter pipes is proportional to the pressure gradient. Therefore, a pressure change from 2 atm to 1 atm, from one end of a pipe to the other, will produce the same flow rate as a pressure change from 12 atm to 11 atm, as both are a change of 1 atm. Prior inventions would maximize flow by maximizing the pressure gradient. Thus for example a pump, or pumps, would be applied across a membrane to increase the pressure gradient across it.

In contrast, for appropriately designed nanojacks, flow across a nanojack can be increased with a decrease in the pressure gradient across it, in combination with a properly chosen absolute pressure.

Minimizing the energy needed to achieve a given flow rate, or maximizing the flow rate given an energy input, can be an important consideration, as for example, in low-cost water purification. The financial cost of energy usage can be crucial to the economic feasibility, marketability, or utility of a device and/or its ability to compete with other means of purifying water. This can be the case, for example, in desalinating water for the population of a metropolitan area. In situations in which energy supply is limited, such as when powered by solar energy, or as in refugee camps or in rural areas, lowering the energy needed for desalination may permit sufficient water to be made available. Many other industrial processes require the separation of one substance from another, and many separations processes depend on constructing very narrow nanochannels which hinder the transport of one species, while facilitating the transport of another species.

According to the embodiments of nanojack design disclosed herein, devices can be constructed in order to optimize flow rates for a given substance at a given energetic cost. For example, a nanochannel can be selected for a separations process for which the periodicity of the potential minima of the nanochannel can be properly mismatched to the spacing of the contained substance particles at expected operating conditions.

Figure 8:
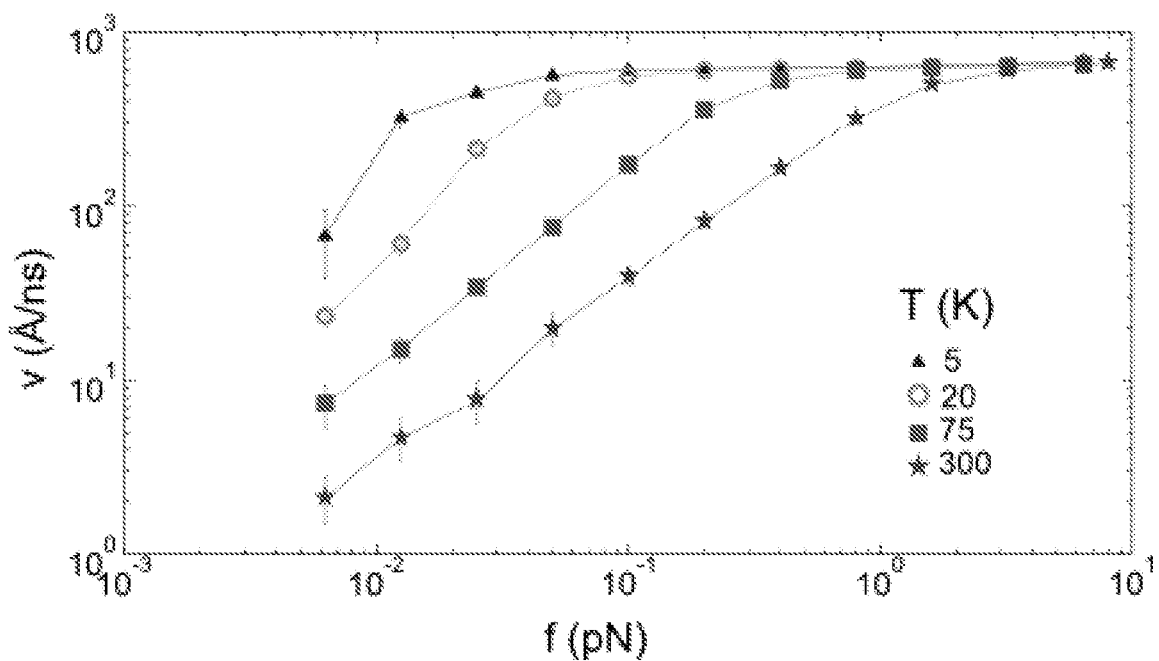
FIG. 8 plots a performance metric v versus a variable f that is a stand-in for pressure gradient.

An inherent feature of nanojacks is that the contained substance has properties that are not present in its isolated state. For example, though solid when isolated, when comprising a nanojack designed according to the methods herein, the material can flow or be transported through the nanojack. Thus, nanochannel transport devices can utilize temperatures not previously considered as viable operating temperatures for flow. For example, bulk water freezes at or near 0 degrees Celsius at standard pressure (about 273 K at 1 atm). Yet, flow of water molecules can occur through nanojacks at temperatures well below 0 degrees Celsius. FIG. 8 shows results from molecular dynamics simulations that were performed of flow of water through a carbon nanotube. FIG. 8 plots a performance metric v versus a variable f that is a stand-in for pressure gradient.

Not only do nanojumps move at low temperatures, nanojump speed can be enhanced at low temperatures. For example, in FIG. 8, at equal pressure gradient, as the temperature decreases, the flow rate increases, even at temperatures well below the bulk freezing temperature of water (see the highest curve, which is at a temperature of 5 K). In the conventional view of nanochannel transport, higher temperatures allow flow more readily, or are thought to allow flow more readily, as, for example, by particles acquiring thermal energy to have enough energy to overcome surface roughness within the nanochannel. However, nanojacks can operate more advantageously at low temperatures. At low temperatures, thermal fluctuations are reduced. Consequently, nanojump transport can be better effected without the stochastic perturbations of thermal energy.

When used for transport, for example, desalination or other chemical separation, low-temperature operation can consume less energy for equal flow rates compared with higher temperature operation. At low temperatures, nanojumps move steadily without slowing or stochastically reversing directions, as seen in the comparison FIG. 15, which shows trajectories of nanojumps versus time. In the bottom panel, at high temperatures, nanojumps sometimes reverse direction. In the top panel, at colder temperatures, nanojumps move steadily in one direction, producing faster flow. In a preferred embodiment in which transport is required to be as fast as possible, operation at low temperatures is a novel aspect of this disclosure.

At low temperatures thermal fluctuations are reduced. Consequently, low temperatures provide certain other advantages in operation. For example, when used for metering of single molecules or small numbers of molecules, the operation at low temperature reduces thermal fluctuations that would otherwise yield less precise dispensing. For nanojacks where static nanojumps are employed, at low temperatures, thermal fluctuations are reduced, consequently positioning of contained particles can be carried out more precisely than at higher temperatures.

A substantial advantage of the compositions and methods herein, is the array of conditions that can be controlled in order to design more advantageous nanofluidic and nanotechnological devices. For example, temperature of the substance, surface roughness of the internal lumen of the nanochannel, interior periodicity of the nanochannel, nanochannel radius or diameter, absolute pressure of the substance, ratio of number of molecules or atoms of the substance to a number of potential energy minima location along the nanochannel, degree of nonlinearity in the substance particle interaction, and any means for effecting the same all form considerations in nanojack design. For example, increasing the flow of the substance through the nanochannel can be achieved by at least one of decreasing temperature of the substance, increasing the width of nanojumps by choosing nanochannels with more closely spaced atoms, increasing the applied absolute pressure (viz., absolute rather than gradient pressure), and increasing an absolute value of S, as defined herein. In some embodiments, a preferred potential may not be available in a desired set of nanochannels. In such cases or alternatively to using the nanochannel potential alone, an external field can be applied. For example a spatially varying electric field can be applied thus subjecting the contained substance within to a spatially periodic field. The strength and wavelength of externally imposed fields is chosen according to the methods of nanojack design disclosed herein.

Arrays of nanojacks can be assembled. In some applications, large quantities of fluid are desired to be transported. In other applications, surfaces can be preferably patterned, for example, by molecular-scale deposition in parallel. In general, in many applications, using multiple nanojacks in parallel affords economic benefits. Nanojumps can be formed within nanojacks where no nanojumps were previously present. Some methods of excitation can be optical, electronic, or thermal. For example, nanojumps can be formed in such manner to serve as a basis of transport. In other cases, such nanojump formation can serve as a basis for detecting photons or other impinging particles. Additionally, nanojumps can also be excited in such manners in nanojacks where nanojumps are already present. Though not limited by theory, a description of the energy to create new nanojumps can be estimated by the FK model theory.

Arrays of only two or three nanojacks, or arrays containing more such as four, ten, twenty, a dozen or dozens, one hundred or hundreds, thousands, millions, billions of nanojacks or more can be assembled. Such arrays may serve to scale up transport. In other cases the arrays are constructed such that the contained substances of the nanojacks can interact, combine, or chemically react. For example, if two nanojacks contain two different amino acids, then the nanojacks can deliver their contents into a common solution, where the order of delivery is controlled such that the amino acids yield a polymer with a desired sequence of the two amino acids.

The control of electrical fields by creating or destroying nanojumps is also provided. For example, when the contained substance is composed of charged particles, electric fields generated by the charged particles vary between regions of nanojumps and regions without nanojumps.

In some embodiments, nanojumps can form in narrow nanochannels other than single-file nanochannels. The novel features of the disclosure herein arise, in part, from the engineered inhomogeneous distribution of density of the contained molecules along the nanojack. When substance particles are not sufficiently restricted such that they form a single-file arrangement, similar inhomogeneities to those described for single-file nanochannels are possible. Compositions can be formulated, designed and implemented employing the methods of nanojump design disclosed herein. Methods for design can use or be based on the methods of nanojump design disclosed herein.

In other embodiments, such as with chiral nanotubes, the novel features disclosed herein arise without the presence of nanojumps—for example, single-file substance flow through a chiral nanotube may be tuned by changing external conditions such as pressure. Changes to the absolute pressure can alter the trajectory of substance particles and thus the flowrate As disclosed herein, through simulations and application of theory by someone suitably skilled in the art, appropriately designed nanojacks and operating conditions can be determined. While not limited by a particular analysis or theory, the methods use or are guided by predictions of the theoretical model, or effective equivalents, or can use or be guided by the results of numerical simulation, numerical computation, or other forms of analysis that can be performed for one or more particular situations, or selected from a tabulation of previously performed analysis, experimental results, or observations.

Nanojack Compositions

For a subset of single-file nanochannels, whose walls follow particular structures, the contained substance, in combination with the particular structure of the nanochannel wall, and when present as a chain of sufficient length, form the composite structure of a nanojack. The sufficient length is to incorporate chains of contained substance that are at least as long as the length of at least one nanojump. As appreciated by those in the art, the length, L, of nanojumps can be estimated by, but not limited to, the Frenkel-Kontorova model theory. The nanochannel structure is preferably selected to achieve a desirable number of nanojumps in the nanojack. In cases where a nanochannel is too smooth to form nanojumps, nonlinearity of particle interactions can be used to form nanojumps.

A nanojack is fabricated preferably such that substance particles arrange in single file through the nanochannel. However, in some cases, nanojacks can still be formed by wider channels, so long as nanojumps and the nanojump mechanism of transport are sufficiently enabled. Any suitable nanochannel can be used. Suitability is based on the formation of nanojumps. Highly preferred nanochannels include those with a repeating motif along the length of the nanochannel. As the atoms of the nanochannel closest to the contained substance are expected to interact most strongly with the contained substance, consequently in some embodiments it is these atoms that should be in the form of a repeating motif along the length of the nanochannel, while more distant atoms can deviate from periodicity. In some cases the repeating motif can be directly identified as comprised of a repeating subset of atoms. In some cases, the periodicity arises from nanochannels that have a structure that is invariant to discrete displacement along the nanochannel axis with or without rotation about the axis. In other words, as will be appreciated by those in the art, the lattice of atoms comprising an inner circumference of a nanochannel can be invariant to particular translations or translations plus rotations. In this way, entire parts of a nanochannel can be tiled by a motif. In some cases, the nanochannel can be composed of a long polymer or other long molecule that is wound around, in some instances as a helix, in a repeating form. In cases where the nanochannel is not sufficiently periodic to form nanojumps at rest, nanojumps can still be formed transiently by delivering an impulse to the substance particles and when the substance particle interaction is sufficiently nonlinear. In some embodiments, the nonlinearity of force between contained substance molecules is critical to the formation of nanojumps, and the repeating motif of the nanochannel is of secondary importance or of negligible importance. The mathematical theory of the Toda model can be applied to determine the importance of nonlinearity.

The nanochannel preferably comprises an open-ended or closed-ended nanochannel. In certain embodiments, a nanochannel is formed from a crystalline unit cell, such as a carbon, silicon carbide or boron nitride. A preferred material composition of a nanochannel comprises a nanotube. Preferably, the nanotube comprises a single-walled, armchair or zigzag type nanotube having an internal diameter chosen to sustain single-file arrangement of the contained substance. Preferably the nanotube has an internal diameter that is both (a) larger than the diameter of a single substance particle of the contained substance and two atomic radii of the appropriate constituent of the nanotube wall, and (b) smaller than twice the diameter of a single particle of the contained substance and two atomic radii of the appropriate constituent of the nanotube wall, such that neighboring substance particles cannot switch places; preferably the nanotube has an internal diameter that is both (a) larger than the diameter of a single molecule of the contained substance and two atomic radii of the appropriate constituent of the nanotube wall and (b) smaller than twice the diameter of a single molecule of the contained substance and two atomic radii of the appropriate constituent of the nanotube wall.

Double-walled and multiwalled nanotubes can also be used. In some embodiments, the single-file nanochannel is a peptidic nanochannel that is formed by a helical winding of a polymeric peptide, such as, but not limited to, gramicidin.

In some exemplary embodiments, the periodicity arises from an external field. For example, an electric field can be applied to a nanochannel, imposing a periodic field on the contained substance within, thus providing a desired degree of periodicity for nanojump formation.

Too great a number of impurities in the walls of the nanochannel, such as for example the undesired substitutions of carbon atoms with a different chemical element, may hinder or prevent the formation of nanojumps. Consequently, it is preferred that the occurrence of impurities should be low enough that impurities are separated by approximately at least the width, L, of a nanojump. The effect of impurities on the formation of nanojumps can be determined by a molecular dynamics simulation by one skilled in the art. In some cases, the error rate cannot be lowered beneath a required threshold, and the effect of the impurities is sufficiently severe, so that such single-file nanochannels are excluded from many embodiments proposed here, as they do not readily form nanojumps.

The nanochannel cross-section can have a substantially cylindrical shape, or any other suitable shape. In other words, the internal cross section of the nanochannel normal to the axis of the nanochannel extending from inlet to outlet of the nanochannel can have a circular, oval, polygonal (e.g., square, rectangular, triangular, hexagonal, etc.) or irregular shape.

The means to fabricate single-file nanochannels will be appreciated by those in the art, and can be accomplished in a variety of ways. For example, carbon nanotubes can be formed by chemical vapor deposition.

In some cases, the contained substance can be incorporated within growing nanochannels during fabrication.

Fabricated single-file nanochannels with closed ends can have one or both ends chemically opened, so that bulk substance can then be incorporated within. For unfilled single-file nanochannels with one or both ends opened, the opening or openings can, for example, be placed in contact with the bulk substance, for instance by physical submersion, so that substance is drawn into or made to enter the lumen. For example, pressure or temperature can be used, or electrical charge distribution of the walls of the nanojack, or near the ends of the nanojack. A current can be imposed on the nanotube. Or, the electrical charges can occur as charged or partially charged atoms on side groups or moieties on the channel walls. In a further example, electrical current passed from bulk substance through the nanochannel wall or the reverse can draw bulk substance into the nanochannel.

In cases where the diameter of the nanochannel varies along the axis, the condition for single-file nanochannels must either be met for the length of the channel, or, the single file regions must be sufficiently long as described herein. For instance, many metal-organic frameworks (MOFs) have short narrow segments where contained substance are restricted to single-file, alternating with larger regions where contained particles are not so restricted. Such MOFs are excluded from the invention described herein unless the single-file sections are long enough to support at least one nanojump.

In a preferred embodiment, the contained substance is water. The molecular diameter of a water molecule in bulk is about 2.75 angstroms. In a preferred embodiment the nanotube has a diameter sized to accommodate a single file chain of water molecules; in a preferred embodiment the nanotube has a diameter that is both (a) larger than the diameter of a single molecule of water and two atomic radii of the appropriate constituent of the nanotube wall and (b) smaller than twice the diameter of a single molecule of water and two atomic radii of the appropriate constituent of the nanotube wall; in a preferred embodiment the nanotube has a diameter between about 5.4 angstroms and about 10.2 angstroms.

Particular preferred inorganic molecules include, but are not limited to, metals, including copper or gold, semiconductor molecules such as silicon or gallium, doping molecules, diatomic molecules such as hydrogen, noble gases, radioactive elements, or transition metals. The contained molecules can be naturally occurring or man-made materials. Other preferred molecules include organic molecules such as, but not limited to, small molecules such as methane, alcohols such as methanol, hydrocarbons such as the alkanes, amino acids and nucleic acids including the biomolecules composed of amino acid residues and nucleotides or nucleosides, namely proteins, peptides, polypeptides, and nucleic acids.

Nanojumps within Nanojacks

Nanojumps imbue the nanojack with novel properties. For example, the transport of a contained substance below its bulk freezing point disclosed herein is facilitated by nanojumps. Additionally, when nanojumps are not present, transport can be significantly limited or in some cases ceases completely. The number of, and consequently, density of, nanojumps can be altered by external means such as an applied pressure or voltage. A means for calculating the number and density of nanojumps is further disclosed herein.

In a preferred embodiment, the number of nanojumps in a nanojack is dependent on the difference in a characteristic spacing of the substance relative to a characteristic periodicity of the nanochannel potential. In general, when the two distances are equal, then no nanojumps are present. In general, with an integral number of nanochannel periods for each molecule of contained substance, there are no nanojumps. Methods for determining the number of nanojumps are described herein.

In some nanochannels, the potential energy minima locations in the nanochannel are associated with the hexagonal ring structure of a nanotube. For example, for a single-walled armchair-type carbon nanotube, there can be two potential energy minima locations for each carbon ring. A water molecule generally occupies positions every other potential minima location if the number of water molecules equals the number of carbon rings in the nanotube, giving S=0. In this case, water flow through the nanotube may be hindered. Thus, in some preferred embodiments, the number of molecules or atoms of the substance in the nanochannel at a given time is not set to an integral multiple of the number of potential minima.

In other embodiments where the nanochannel is exceedingly smooth or nanojumps are otherwise not present, nanojumps may be created through external means such as by a pressure pulse, if the nonlinear interaction of the force between contained substance molecules is sufficiently large In one embodiment of nanojumps, the contained particles in the region of the nanojump are spaced more closely than outside of the nanojump, and are called compression nanojumps. In another embodiment of nanojumps, the contained particles in the region of the nanojump are spaced farther apart than the particles outside of the nanojump, and are called expansion nanojumps, though nanojumps are not bound by terminology. If compression nanojumps are present, then decreasing the particle spacing further consequently can create additional nanojumps. On the other hand, increasing the particle spacing can lower their number. Conversely, when expansion nanojumps are present, then the opposite would hold.

The length of the nanojump is set by the combined properties of the substance and nanochannel and can be adjusted by external conditions such as the absolute pressure. The nanojump length can be predicted by the results of the FK model theory presented known to those in the art or by the results of numerical simulation. The characteristics of the nanojack will depend upon the length of the nanojump. For example, in short nanojumps the change in density occurs over a smaller distance, and therefore can more readily facilitate well-controlled discrete metering.

In general, in narrower nanotubes, nanojumps are shorter. In the (4,4) CNT isolated nanojumps are approximately 20 water molecules long whereas in the (6,6) CNT isolated nanojumps are approximately 150 water molecules long.

In general, for a given applied force, longer nanojumps will transport contained substance at a higher speed, while shorter nanojumps will transport contained substance at a lower speed. Additionally, in general, the lowest force at which transport will occur is lower for longer nanojumps.

It is expected that nanojumps can be detected by appropriate means. Several possible experimental tests are disclosed herein. Other tests, not enunciated herein can be applied to detect the presence of nanojumps. One or more of these tests can be preferably conducted at cold temperatures, in the range k_B T~<E_PN, where thermal noise is reduced. As appreciated by those knowledgeable in the art, k_B T is the thermal energy and E_PN is the Peierls-Nabarro energy.

For instance, nanochannels filled with contained substance can in some cases be probed for energy excitations in an energy range determined from the defect creation energy known to those in the art. For example, optically responsive substance can be excited by impinging light to form nanojumps. If energy excitations are found in the range predicted by theory, then the contained substance must be arranged into chains of sufficient length, and the filled nanochannels are thus determined to be nanojacks. If the contained substance were not formed into chains of sufficient length, than the excitations in the predicted range would not be possible.

In another test, if a series of nanojumps are expected to be present and separated by a distance 1, then impinging particles can in some cases form interference patterns associated with this length scale.

In a further test, the presence of nanojumps can in some cases be detected by their contribution to the system heat capacity.

Nanojumps facilitate transport of the contained particles along the nanochannel axis, and so transport at low applied forcing, f~f_PN, can occur if nanojumps are present. As appreciated by those knowledgeable in the art, f_PN is the Peierls-Nabarro force.

By fabricating different types of nanojacks, experimental measurements can be compared to flow rate predictions using molecular dynamics (MD) methods or theory as known by those in the art. Sufficient agreement with theory or simulation strongly indicates transport via nanojumps.

As nanojumps can permit the metering of discrete quantities of contained substance from the tip of the nanojack, such metering can in some cases be detected as the metered substance exits the nanojack, or passes by a detector, or contacts an opposing surface or detector. Discrete metering of substance into the space outside the nanojack can be detected by a photodetector, laser, or electrical circuit, or other means. The discrete metering of contained substance can be detected by the accompanying discrete metering of electrons in the channel walls. Discrete metering sufficiently in agreement with theory strongly indicates transport via nanojumps.

Nanojump-Mediated Transport within Nanojacks

The substance being transported in some important applications is water, but is not limited to water. In other instances, the substance being transported can be a bulk solid at the operating temperature. In a preferred embodiment the substance being transported is comprised of small molecules; in one preferred embodiment the substance being transported is water; in one preferred embodiment the substance is copper; in one preferred embodiment the substance is silicon; in one preferred embodiment the substance is gallium; in one preferred embodiment the substance is hydrogen; in one preferred embodiment the substance is gold; in one preferred embodiment the substance is a transition metal; in one preferred embodiment the substance is an amino acid; in one preferred embodiment the substance is a nucleotide. In a preferred embodiment the substance being transported is a large molecule or polymer; in one preferred embodiment the substance is a polymer; in one preferred embodiment the substance is a peptide; in one preferred embodiment the substance is a DNA strand; in one preferred embodiment the substance is an RNA strand; in one preferred embodiment the substance is a polypeptide; in one preferred embodiment the substance is a protein; in one preferred embodiment the substance is a quantum dot.

Contrary to conventional understanding of nano-transport, nanojumps provide a means for increasing particle transport within a nanochannel, for example, by increasing the absolute pressure or by decreasing the temperature, even to values below the freezing temperature of the bulk substance (at standard pressure, 1 atm). In one preferred embodiment the temperature of the substance within the nanotube is about 300 K or below; in one preferred embodiment the temperature of the substance within the nanotube is about 200 K or below; in one preferred embodiment the temperature of the substance within the nanotube is about 100 K or below; one preferred embodiment the temperature of the substance within the nanotube is about 75 K or below; one preferred embodiment the temperature of the substance within the nanotube is about 50 K or below; one preferred embodiment the temperature of the substance within the nanotube is about 20 K or below; one preferred embodiment the temperature of the substance within the nanotube is about 10 K or below; one preferred embodiment the temperature of the substance within the nanotube is about 5 K or below. The number of, and thus the density of, nanojumps within a nanojack can be subject to external control. Nanojumps at low density within nanojacks, in other words widely spaced nanojumps, can facilitate discrete transport. Each widely spaced nanojump discretely transports one or a few molecules or increments in position of the contained substance. In this way, by controlling the frequency of nanojump passage, the number of molecules or the incremented distance can be counted out. On the other hand, transport increases as the number of nanojumps increase. Thus, when nanojumps are closely spaced, transport of contained substance can be quicker.

Figure 9:
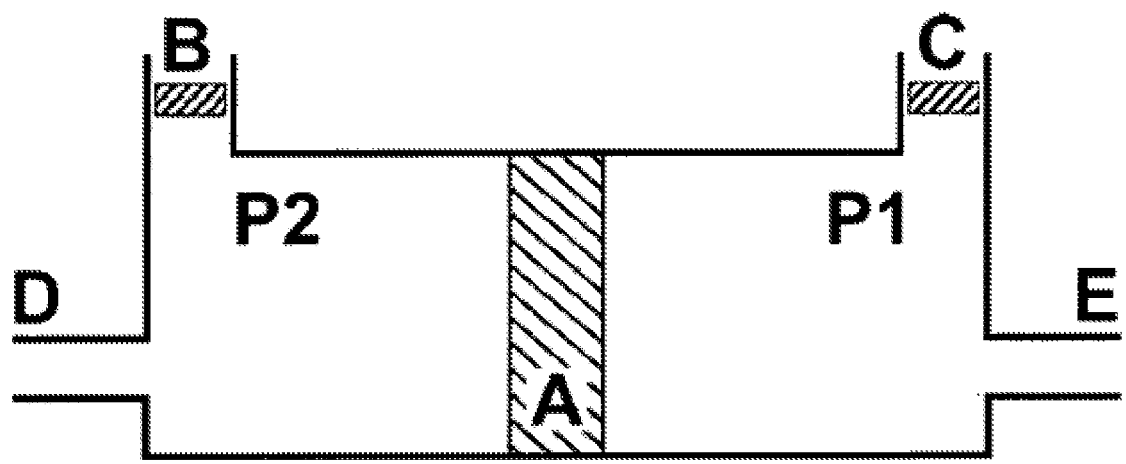
FIG. 9 is a schematic of an example of part of a nanochannel device. The substance flows from the region labeled with pressure P2 to the region labeled with pressure P1 through nanochannels within region A. There is the facility to adjust the pressure P2 with device B and also to adjust the pressure P1 with device C. That is, even when the pressure difference P2−P1 is kept constant, the absolute pressures P1 and P2 can be adjusted. There is also the facility to add or remove substance shown schematically as inlet/outlet D and inlet/outlet E.

FIG. 9 is a schematic of a system that can apply a range of absolute pressures. The pressure gradient through the nanochannels comprising A can be kept relatively constant for different values of the absolute pressure. In this way, the number of nanojumps in the nanochannels can be changed. Consequently, the flow rate and the degree of discreteness of transport events through A can be changed.

For applications for discrete metering, as for example in the deposition of individual atoms or molecules onto a substrate, the metering of the number of molecules does not require that the mechanism driving the molecules through the nanochannel be switched on and off for each molecule to be transported. Rather, nanojump spacing is effectively the switch that turns on and off the transport.

Some embodiments provide the metering of transport by a discrete amount by passage of a nanojump through a nanojack, and this discrete amount is intimately related to the structure of the nanochannel, as described in greater detail herein.

Figure 14:
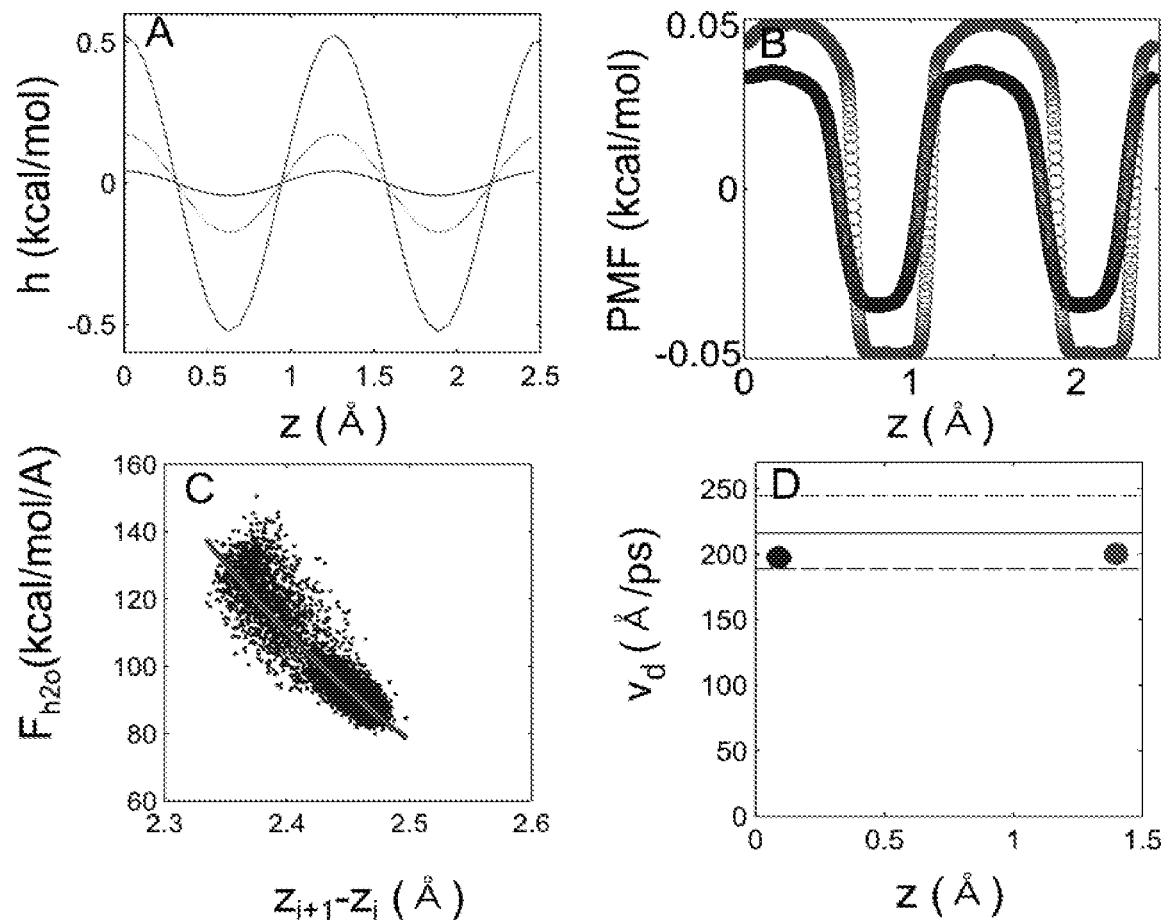
FIG. 14 shows various modeled data for a water-water interaction in the (4,4) CNT where nonlinear interactions between water molecules are modeled by the Toda potential.

In some embodiments the interactions between the molecules of the contained substance are not adequately modeled by the linear approximation of the force as in a usual formulation of the FK model. In these cases, the nonlinear or anharmonic character of the inter-particle interaction needs to be modeled and incorporated into the modeling of the nanojack, and in methods for choosing operating conditions. We have developed novel methodologies to incorporate the nonlinearity of the force interaction between particles into our methods to analyze and design, and find operating conditions for nanojacks. For example, we fit the Toda potential to the nearest-neighbor interaction between water molecules, and used this potential in the FK model, in place of the linear force typically used, to analyze flow through a (4,4) carbon nanotube with S=+1 at 20 K. To find the nonlinearity characterizing the force interaction, we measured the force between adjacent water molecules as a function of the separation of the oxygen atoms, as shown in FIG. 14 panel C which presents the force as measured in kcal/mol/angstrom versus the separation in angstroms. The data from the numerical simulation measurements is plotted as data points. These points are well fit by the Toda potential, shown by the line through the data. The coefficients from this fit are used with the combined Toda-FK model to predict the flowrates $v\_d$. The nanotube potential representing the (4,4) nanotube in the FK model, is shown as the light line in FIG. 14 panel A. Two additional potentials we generated by multiplying the potential by three (the curve with the largest amplitude in FIG. 14 panel A) and by ¼ (the curve with smallest amplitude in FIG. 14 panel A), as shown as a function of distance z along the nanotube axis. The potential of mean force, PMF=-$k\_B$ ln rho, where $k\_B$ is Boltzmann's constant, ln is the natural logarithm, and rho is the local particle density, is shown in FIG. 14 panel B for the two cases of the potential as multiplied by three (larger amplitude curve) and as multiplied by ¼ (smaller amplitude curve). The potentials shown in FIG. 14 panel A are used in the FK model together with the nonlinear Toda potential in a combined Toda-FK model. In FIG. 14 panel D, the combined Toda-FK model prediction for the flow speed $v\_d$ as a function of the peak-to-peak amplitude of the nanotube potential, is shown. The solid horizontal line is the prediction for the (4,4) nanotube, where the dashed lines are the uncertainty in the prediction due to the fit of the Toda potential to the data, as shown in FIG. 14 panel C. The left and right dots are for the potential multiplied by ¼ and by three, respectively. As can be seen, both dots are within the error bounds for the flow speed as predicted by the Toda-FK model for the (4,4) potential. Furthermore, the flow speeds are largely independent of the amplitude of the nanotube potential, in agreement with the Toda-FK model.

In other embodiments, there is advantageous electron transport in the channel walls effected by the motion of a contained substance, or vice versa. As a consequence of discrete transport of substance, and coupling between substance particles and electrons in the nanochannel, discrete quantities of electrons can also be transported. Devices needing electrical power can benefit from harvesting the energy in single-file flows. By placing many nanojumps into a device, their operation in parallel yields a generated current that is roughly proportional to the number of nanojumps, so the amount of electrical power generated can be scaled up.

In other embodiments, nanojacks with stationary nanojumps can transport protons along the chain of substance particles, which can be useful in batteries, fuel cells, and other applications. Such proton transport can be modulated by the number and width of nanojumps, for example, short nanojumps can discourage proton transport.

The substance can be made to move within the nanochannel via a potential difference generated by numerous methods or means. The means can be continuous or delivered in impulses, in which the amplitude of the means varies. Also, a sampling of potential differences that can be used includes:
  (i) a pressure difference between the upstream and downstream ends of the nanochannel,
  (ii) a temperature difference between the upstream and downstream ends of the nanochannel,
  (iii) means by which the flow of electrons through the nanochannel walls induces a flow through the nanojack,
  (iv) means by which a flow external to the nanochannel induces transport through the nanochannel,
  (v) a time-varying electric or magnetic field applied to the contained particles (Rinne et al., Nano Lett. 12:1780 (2012)),
  (vi) sound waves or pressure impulses impinging on the nanojack (Insepov et al., Nano Lett. 6:1893 (2006)).

Nanojack Design

Methods and systems for conveying and controlling the transport of substances through nanojacks are disclosed, wherein the transport occurs by the passage of nanojumps. The methods and systems generate nanojumps and control their number and mobility. In this way, the amount of substance transported through nanochannels can be effected and controlled. As nanojump passage is associated with individual transport events, then widely spaced nanojumps are preferred, in many embodiments, for discrete metering. At high nanojump density, individual transport events get crowded together. Neighboring nanojumps overlap and it is more difficult to discern individual events. Consequently, high nanojump density, in many embodiments, is preferred for high flow rates.

The methodologies presented herein determine or help determine the preferred choices for making nanojacks for particular applications. For a particular application, it can be determined by preference, economic factors, or other factors that a particular element comprising the nanojack or a particular operating condition is to be used. From among the allowable possibilities, the methodologies determine, one, some or all of, but not limited to, the nanochannel, nanojump width, substance, operating pressure, temperature, and amplitude- and time-dependence of applied force, whose combination gives an optimal performance. Computer programs, molecular dynamics simulation, and theory can be used to obtain device operation parameters.

The methodologies used are sometimes termed the "optimization method" or grammatical equivalents.

In some embodiments, a simple estimation procedure is used. In some embodiments, only part or parts, but not the entirety of the detailed procedure described below is used. In some embodiments such procedures using rules-of-thumb or principles derived from or based upon the presentation herein and the FK model theory as known by those in the art.

General MD Methods

Molecular dynamics (MD) simulations can be conducted using acceptable practice. Any suitable molecular dynamics software can be used. In some embodiments, Gromacs, LAMMPS, or NAMD are used. Any standard interaction fields can be used, such as any bonded interaction models, non-bonded interaction models, and coulomb interaction models and methods. In some embodiments, one or more of spring-type bonding models, a 6-12 Lennard-Jones model, and long-range coulomb particle-mesh Ewald (PME) model can be used. In one embodiment, more specific to contained metal atoms, long-range many-body interaction terms are included. Any suitable ensemble can be employed. In one embodiment, the NVT ensemble and periodic boundary conditions (PCBs) are used. When needed, any temperature control method can be used. In a preferred embodiment the Langevin thermostat is used to avoid unphysical artifacts, which can sometimes occur with other thermostats, such as the flying ice cube effect. In a particularly preferred embodiment the Langevin thermostat is applied only along the dimensions perpendicular to the channel axis, to avoid an unphysical slowing of the substance particles. In another embodiment, a Galilean invariant thermostat is used such as the Lowe-Andersen thermostat. In some embodiments only the walls of the nanochannel are thermostatted. In general, results with different thermostats should be compared. When needed, any reasonable pressure control method can be used. In one embodiment a Langevin piston barostat is used. Any reasonable time step can be used. In some embodiments a non-bonded time step of 2 fs and a bonded time step of 1 fs are used. Any reasonable non-bonded cutoff can be used. For some types of simulations, including especially those at low temperatures, a longer than standard cutoff method is used. In some embodiments, a 12 A cutoff is used. Any reasonable method of truncating or smoothing non-bonded interactions near the cutoff distance can be used. In one embodiment a smooth shifting function is used. Any reasonable neighborlist method can be used. In some embodiments, the neighborlist is updated every 10 time steps. In a preferred embodiment the neighborlist is updated every other time step, to reduce neighborlist violations that can occur more frequently than expected in nanochannels. Any method of simulating the nanochannel wall can be used. In some embodiments, rigid-wall atoms are used. In a preferred embodiment, rigid-wall atoms are replaced with a potential energy grid for computational expediency, referred to as the substrate grid method. In a preferred embodiment, the potential energy grid is calculated with a long non-bonded interaction cutoff, for example 15 A or more, to mitigate sharp step forces on substance particles. In a particularly preferred embodiment the non-bonded cutoff length is 25 A or more. Computational efficiency-gains with the substrate grid method can be significant. Simulations times may be reduced in many embodiments by a factor of approximately 2 to 20. Exact increase in efficiency depends on the length of system being simulated. Additionally, when a long cutoff length is used, electrostatic interactions may be computed directly, and for example, no PME may be required. By turning off PME or related methods, simulation times may be reduced by a factor of 2 or more. The exact increase in efficiency depends on the size of the system. Long cutoff lengths are usually impractical for MD simulations as the time required to run simulations increases dramatically with cutoff length. However, using long cutoff lengths does not overburden simulations of many single-file systems containing nanojumps, due to the high aspect ratio of such systems and thus the slower increase in the number of interparticle interactions that must be computed.

When the applied force is large or temperature large, rigid-wall atoms may no longer be appropriate. As is known to those in the art, flexible wall channels may be required when the contained substance begins to move too fast. This can be observed directly, as the channel friction unphysically transitions to a much lower value once the applied force is too large. In these cases, wall flexibility must be included in the simulation models.

Figure 19:
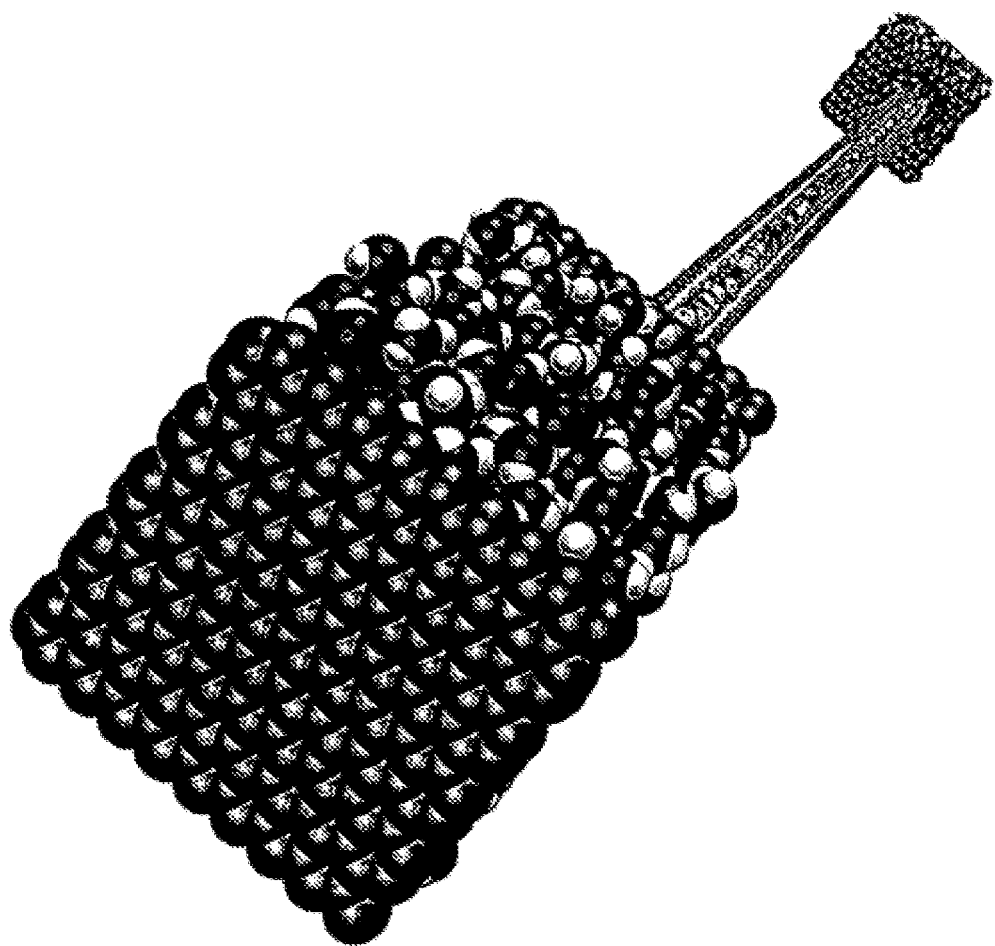
FIG. 19 is a snapshot from MD simulation of water entering a CNT from two reservoirs.

In simulations where it is important to model the nanochannel ends, a geometry such as that shown in FIG. 19 may be used.

Detailed Procedure

In preferred embodiments, more detailed estimation protocols than the simple estimation protocol above are used. In some embodiments molecular dynamics simulations are performed in order to optimize the design considerations outlined above. For example, the molecular dynamics protocol outlined above is used. One embodiment is outlined below.

Figure 10:
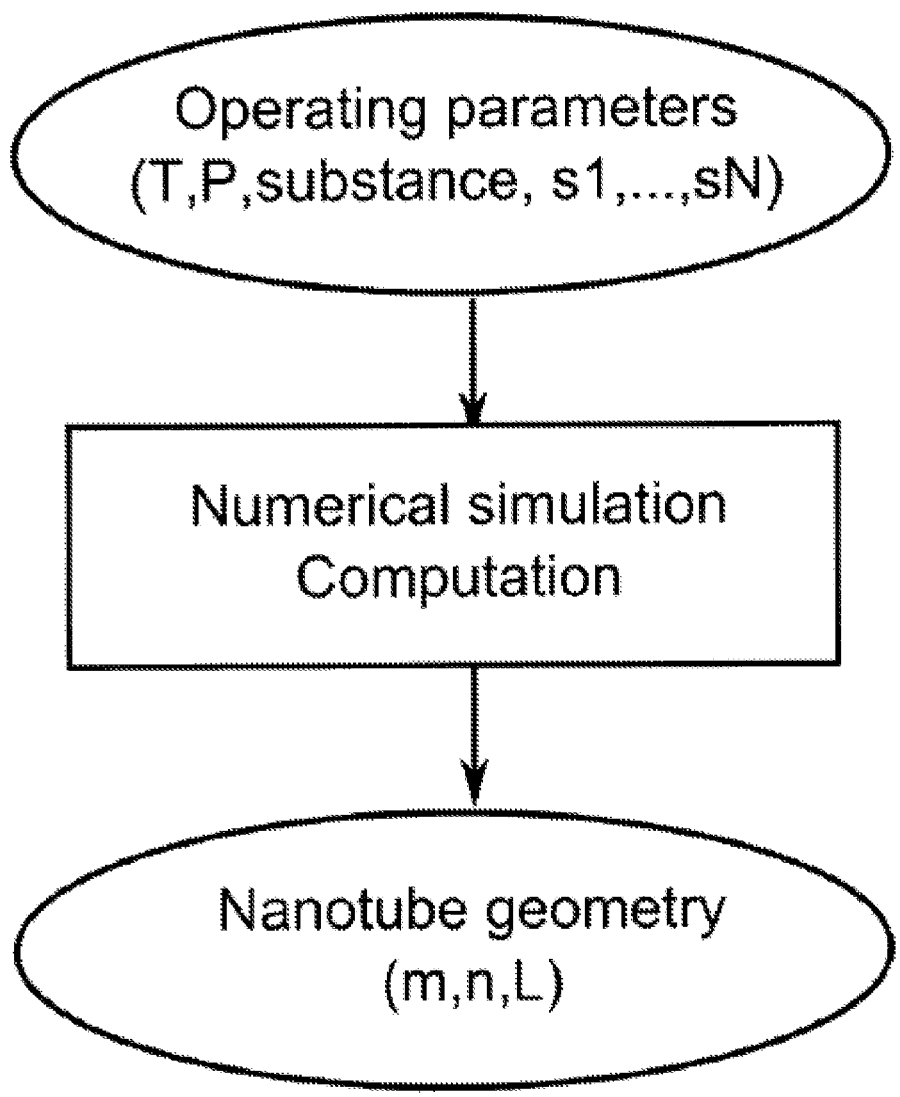
FIG. 10 is a flowchart of an example of how the geometry of nanochannels can be determined in order to achieve desired flow conditions. The controllable operating parameters such as temperature T, pressure P, and other parameters, s1, . . . sN, are modeled using numerical simulation or other mathematical method(s). The output of this algorithmic method yields the parameters to be used in selection of the nanochannels, for example, in the case of flow through carbon nanotubes, the chirality indices m and n, and the nanochannel length L.

In order to design nanojacks to suit particular applications and uses, in particular to find nanojacks that well or best fulfill design objectives, methods for nanojack design are herein disclosed. A schematic outline of a method is shown in FIG. 10. In one method, a set of suitable nanochannels is chosen. In some cases the contained substance is not predetermined by the application at hand, and is also a design parameter. As disclosed herein, nanojump width is a factor that can alter transport characteristics, and nanojump width can be determined from a variety of methods. For example, MD simulations, theory, computer aided theory, or a combination of computer-based methods with or without additional calculations can be employed.

Nanochannels, contained substance, and external conditions are together designed in order to produce a desired density of nanojumps with desired widths. In preferred embodiments the interior potential of the nanochannels is an important factor that determines nanojump density and width. The interiors are characterized for each set of conditions, and may depend on such factors as where the contained particles preferentially reside. For example, if contained particles preferentially lay along the central axis of the channel, then the interior characterization may focus on the portion of the nanochannel near the centerline. In other examples, the contained particles may lay off the central axis and interior characterization then focuses on those regions. Full characterization of nanochannel interior is a multistep procedure, as for example, it may not be known a priori where contained particles preferentially lie, and means must be employed to determine such preferences. However, not all steps of the multistep procedure need to be employed in every case, if for example the preferential positions of contained particles are known or estimated by theory, or through prior experience of the practitioner.

The performance of nanojacks depends in part on the strengths of the interaction between substance particles and the strengths of the interaction between the substance particles and the atoms of the substrate and, in general, on nanojumps width. The strengths of these interactions can be estimated by one suitably skilled in the art. These strengths, in some cases, can be estimated by numerical simulation of the type disclosed herein or other numerical simulation methods known to those in the art, such as quantum mechanical simulations. These strengths depend in part on the relative orientations of the interacting particles.

Alone or in combination with theory, the results of numerical simulation can be used to estimate performance. The performance of different combinations comprising operating conditions, nanochannels, and substances can be compared and the appropriate combination or combinations chosen.

Where Particles Preferentially Lie

For some aspects of the optimization procedures, the approximate mean radial position of the contained particles should be determined. By mean radial position is meant the distance, in a direction perpendicular to the channel centerline or centerline approximation, at which the particles preferentially lie. Mean radial position relates to the effective interior potential amplitude parameter h (described later). Determination of expected mean radial positioning of contained particles can be estimated theoretically, or obtained from simulation. In some embodiments, contained particles are assumed to lie along the centerline. In other embodiments, contained particles are assumed to position as close to the wall as may reasonably be expected, for instance at a distance sigma_pw from the interiormost wall atoms, where sigma_pw represents the length scale of the interaction between substance particle and nanochannel. Sigma_pw and other standard molecular dynamics parameters can be obtained by standard methods or tables. In some preferred embodiments, simulations are performed where substance particles are placed in the interior of an isolated, periodically replicated CNT segment of sufficient length. Simulation conditions are set to approximate values of reasonable operating conditions. The average density of contained particles can sometimes be determined from simulation. In other cases, the density of contained particles can be estimated by calculation. For example, an estimate of the expected density of particles is obtained from contained particle diameter (2*sigma_pp, where sigma_pp is the length scale of the interaction between contained particles) and assuming contained particles lie along the axis, or are closely arranged such that they lie at a distance sigma_pw from the interior wall atoms. In some preferred embodiments, simulations are performed at a variety of contained particle densities to determine the dependence of contained particle density on radial positioning of contained particles. From these simulations a pressure versus density relationship can be calculated by standard methods, which can be later used.

To determine where particles preferentially lie, in some particularly preferred embodiments a finite length nanochannel is simulated in a geometry that is sufficiently similar to device operating conditions and geometries. For example, in a simulation a nanochannel can be immersed in a bath of substance particles to observe how many substance particles enter the nanochannel, and where those particles preferentially lie. In some embodiments, a nanochannel connects to one or more reservoirs of substance particles, so that the opening or openings of the nanochannel is in sufficient contact with the reservoir. In many cases, the simulations can be conducted at expected operating conditions.

FIG. 19 shows a snapshot from a simulation where two water reservoirs were connected to a long (5,5) CNT at standard conditions in order to measure the density of water within the CNT and determine the radial position where particles preferentially lie. An unrestrained graphene sheet is here employed as a piston for each reservoir, though other materials can be used. A constant force is placed on each carbon atom in the grapheme sheet to enforce reservoir pressures of 1 atmosphere. In this case, the system is maintained at 300 K with a Langevin thermostat. This type of geometry can be used to characterize if a nanochannel will fill under a given set of operating conditions, for example, under a given temperature and pressure, can be used to evaluated the ease of filling and, if filled, can be used to determine S.

Figure 11:
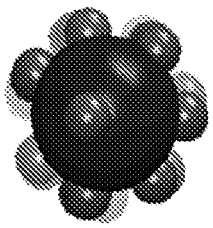
FIG. 11 visualizes water molecule positions and orientations in CNTs of various radii.
Figure 11:
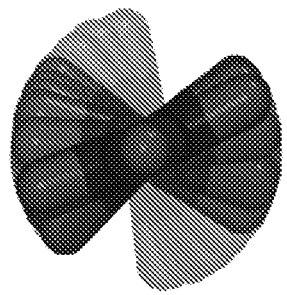
Figure 11:
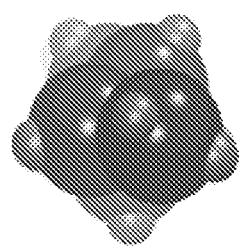

The arrangement of the contained substance in single file flow may be different for different substances and for different nanotubes. Shown in FIG. 11 is a view of the arrangement of water molecules in three different armchair carbon nanotubes as seen peering down the axis of the channel. From left to right are shown the (4,4), (5,5) and (6,6) nanotube. The nanotube structure is not shown. Only the water molecules are shown. The left and right panels employ ball models for the oxygen (larger sphere) and hydrogen. In the (4,4) nanotube, water molecules are located near the nanotube axis, while in the (6,6) nanotube, water molecules are staggered about the axis. The central panel employs the licorice or Dreiding representation to more clearly show the helical winding and alignment of the water molecules along the channel length. Nearer molecules are shaded darker to provide perspective.

Figure 12:
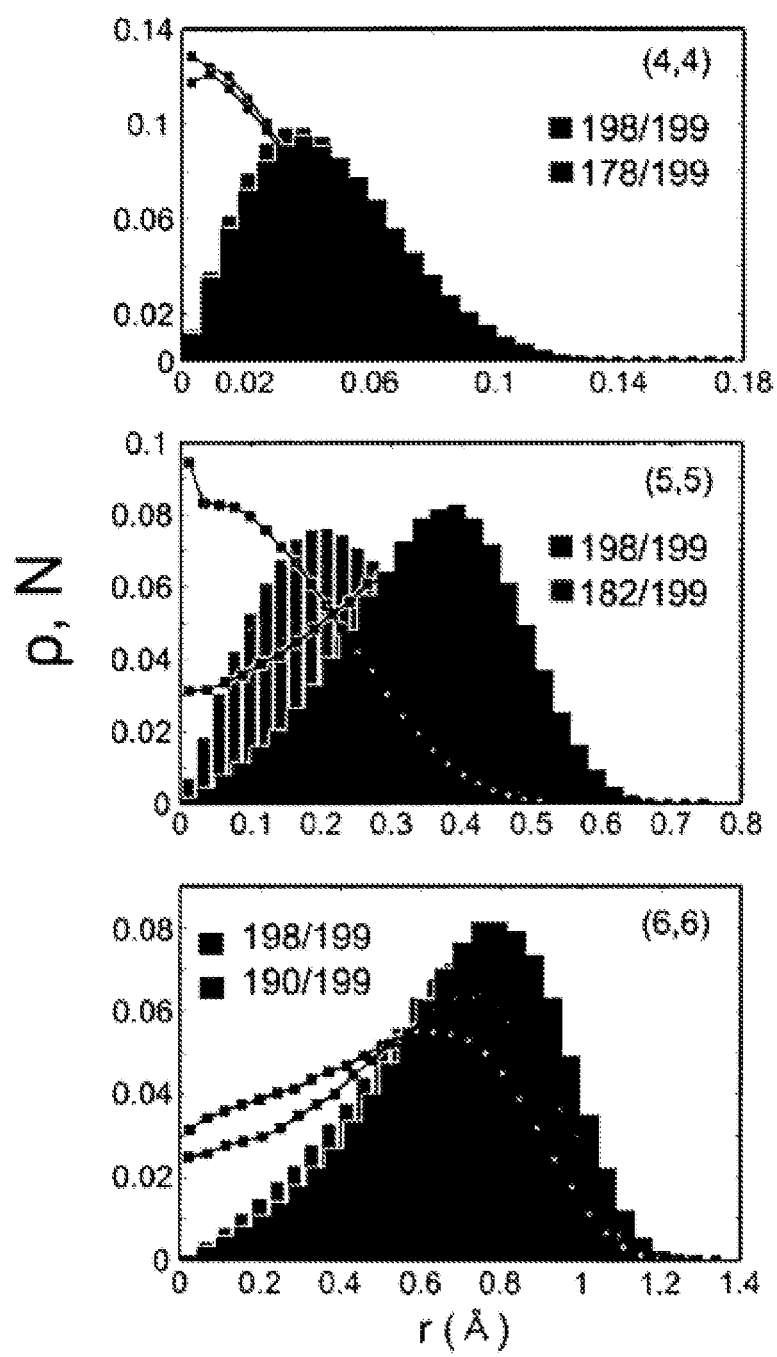
FIG. 12 shows the radial distribution of water molecules within three CNTs, from top to bottom, the (4,4), (5,5), and (6,6) CNTs. The dark-shaded histograms show the radial distribution (frequency of occurrence at each radius considered) at a water density that corresponds to one nanojump in a CNT with a length of 199 hexagonal rings along the axis. The light-shaded histograms show the radial distribution at a pressure near atmospheric pressure. The solid lines show the density of water at each radius. As can be seen water molecules are offset from the central axis (r=0). In the legends are the ratios of the number of water molecules in the CNT to the length of the CNT measured in carbon rings along the axis.

FIG. 12 shows how the radial position of water molecules changes as a function of the nanotube radius and the parameter S.

Interior Amplitude h and Wavelength Lambda

The interior of a nanochannel is characterized by a potential energy surface (PES), U=U(x,y,z). The PES is a scalar function of position and is defined as the potential energy at position r=(x,y,z) within a nanochannel. For example, in many applications the PES is defined as the potential energy of interaction between a test substance particle and the atoms of the nanochannel wall. When calculating the potential between a substance particle and the nanochannel wall atoms, a cutoff distance r_cut may be used where interactions beyond r_cut are ignored. The PES can be defined everywhere inside the lumen of the channel. The PES will be used to obtain the interior channel amplitude, which can be thought of as the bumpiness experienced by the substance particles on average. The PES is also used to obtain the channel wavelength, also referred to herein as the characteristic periodicity of the nanochannel, "interior potential wavelength", "potential wavelength" or grammatical equivalents.

In some embodiments, the amplitude of the PES along the nanochannel axis can be represented by the coefficient h of a Fourier expansion to potential energy. In a similar manner, the wavelength of the PES along the nanochannel axis can be represented by the wavelength of a Fourier mode in a Fourier expansion of the PES. The amplitude h and wavelength lambda can be determined by a computer program or theoretical estimation.

As the molecules of a contained substance travel along the nanochannel, they experience variations in energy arising from the atoms of the nanochannel. In other embodiments, a Fourier analysis of this experienced potential yields one type of measurement of the wavelengths of the interior potential. One of the Fourier wavelengths may have an amplitude much larger than other wavelengths. This wavelength alone, in many cases, can be used as the interior potential wavelength.

In some embodiments, a one-dimensional path through the PES is chosen. The values of the PES along the path are approximated by a sinusoid, the amplitude of which is taken as the coefficient h. In a preferred embodiment the path is chosen based on the likely trajectory of the contained molecules through the nanochannel. The path can be determined from simulation. For example, as the result of molecular dynamics simulations, it can be determined that the oxygen atom of water molecules preferentially are located within an annular region at a certain distance from the nanochannel axis, see FIG. 12. The PES on a cylindrical surface within this annular region can be determined. The amplitude of the potential variations on this surface can be determined and used as the amplitude h.

As a PES, in many embodiments, is dependent on the nanochannel itself, part of the optimization procedure is comprised of determining an optimal PES for the application at hand. Nanochannel choice affects many factors, directly or indirectly, such as channel wavelength lambda, channel bumpiness h, the interior channel chemical potential, density of contained particles, and an important optimization parameter, the nanojump width.

When external potential fields are imposed on contained substance, such fields can be included in simulations. In such cases, the values of h and lambda will be determined, in part, by the external potential field.

Importantly, it is the combination comprised of the nanochannel and substance that constitutes the composite composition nanojack. In general, the choice of operating conditions, nanochannel and contained substance will determine the properties of the nanojack. Methods to choose the operating conditions, nanochannel and contained substance, as appropriate, for desired performance are disclosed herein. Some qualitative guidelines can be given in particular cases, for example, in cases in which the substrate wavelength is less than the average contained particle spacing, operating under a set of fixed operating conditions. When there is one particle for an integer number of periodically spaced minima determined from the PES, then the flow tends to be slower and fewer nanojumps are present than in cases in which there is not. When the ratio of the number of particles to the number of PES wavelengths, is nearly intermediate between two ratios of the form $1/m$ and $1/(m+1)$, where m is any positive integer, than, the flow tends to be faster as there are more nanojumps present. In general, as described herein, an important parameter governing the performance of nanojacks is the ratio of contained particle spacing and a wavelength determined from the PES, lambda.

In one embodiment, the PES is evaluated in the interior of a channel by a computer program. The PES is calculated using a potential of interaction between substance particles and wall atoms that is the same as, or sufficiently similar to, the non-bonded interaction used in MD simulations. A cutoff distance r_cut can be used, outside of which the interaction is neglected. The computer program calculates the PES at a sufficient number of points within the interior using the test particle method, or variation thereof. In the test particle method, the positions of the atoms comprising the nanochannel wall are used to compute the potential energy at points (x,y,z) within the nanochannel lumen. A sufficient length of nanochannel is used, or a basis of replication is used, so as to reduce the influence of end effects. In a preferred embodiment, when the interaction model sufficiently matches the MD simulation, and if the PES is computed at equivalent points, then the PES here can be used in the substrate grid method in MD simulations.

In one embodiment, a small number of interior points is used to estimate the PES. A particle of the working substance is positioned at the center axis of the nanochannel and moved through a collection of points along the axis in order to produce a one-dimensional PES map on, or very near to, the central axis. In such embodiments, the PES is one-dimensional, making straightforward the determination of the characteristic amplitude and wavelength of the potential.

In some embodiments, the PES is estimated as a theoretical estimate, rather than using molecular dynamics simulation. As with methods using MD simulation, the theoretical estimate can be used to determine the potential wavelength and amplitude, among other quantities.

For example, the atoms in the nanochannel wall may lie on a series of circumferential rings, and the density of atoms can be averaged, or smoothed, over such rings. The appropriate potential wavelength and amplitude from this smoothed potential can determined. After smoothing, the potential does not vary in the circumferential direction. In some cases, the variation of the amplitude along a path aligned with the nanochannel axis approximates a sinusoidal curve. In order to have a simple enough potential for a theoretical approximation, the averaging can be done over the atoms collected into other groupings, for example those that lie along rings that are not simple circumferences, but lie at an angle. In another example, the PES along particular trajectories yields the appropriate values of wavelength and amplitude. With these and similar approximations, the PES can be estimated without using MD simulation.

In some preferred embodiments, a test particle is moved through the interior volume of the nanochannel, on a particular trajectory, over a defined two-dimensional surface, or over a plurality of trajectories and surfaces in order to generate statistical averages. Any type of trajectory or surface can be used which sufficiently represents the nanochannel interior. The trajectory or surface should incorporate those points in space where the contained particles preferentially lie. In some embodiments, the test particle is moved over the surface of one or more cylinders. If one cylinder is used, the radius of the cylinder is chosen equal to a suitable expected average radial position of the substance particles (for example, as obtained above).

A variety of methodologies to determine h and the wavelength of the PES can be used. In one embodiment h is one half the peak to trough amplitude over a cylinder centered on the axis with a radius equal to the expected average radial position of the contained substance though in some cases the h is the peak to trough amplitude.

Figure 5:
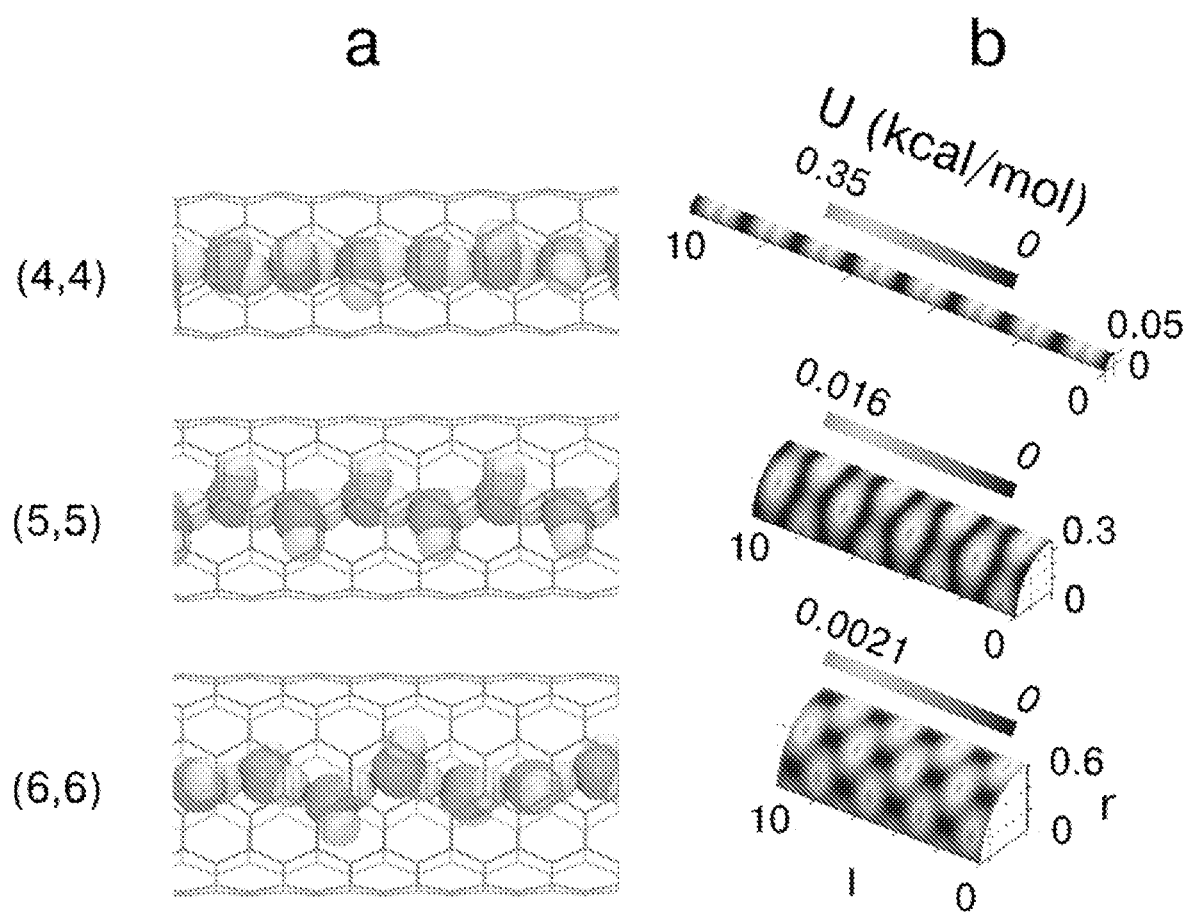
FIG. 5 depicts water in armchair CNTs with cylindrical sections of the PES.

Shown in FIG. 5 in panel a, from top to bottom, are short segments of a view of water in a (4,4), (5,5), and (6,6) carbon nanotube. From numerical simulation, the mean radial position of the water molecules is determined. Shown in panel b, from top to bottom, are the potential energy surface evaluated at the mean radial position of the water molecules for the (4,4), (5,5), and (6,6) carbon nanotube for the cases shown in panel a, namely S=−1 at 1 K. The PES is shown over a short length of a quarter of the cylindrical surface. In each case the axial distance, labeled as 1, covers 10 angstroms. The radius r of the cylindrical surface is labeled in angstroms. The amplitude of the PES is shaded according to the scales shown. For example the shading scale for the (4,4) CNT extends from 0 to 0.35 kcal/mol.

In one embodiment h is the mean peak to trough amplitude evaluated along lines parallel to the channel axis at a radial position corresponding to the expected mean position of contained particles, at a sufficient multitude of angles theta, where theta is the polar angle in the cylindrical coordinate system aligned with the channel axis.

In many preferred embodiments, PESs are computationally inexpensive to determine and consequently can be precomputed for common nanochannels and other nanochannels.

Particle-Particle Interaction

Figure 22:
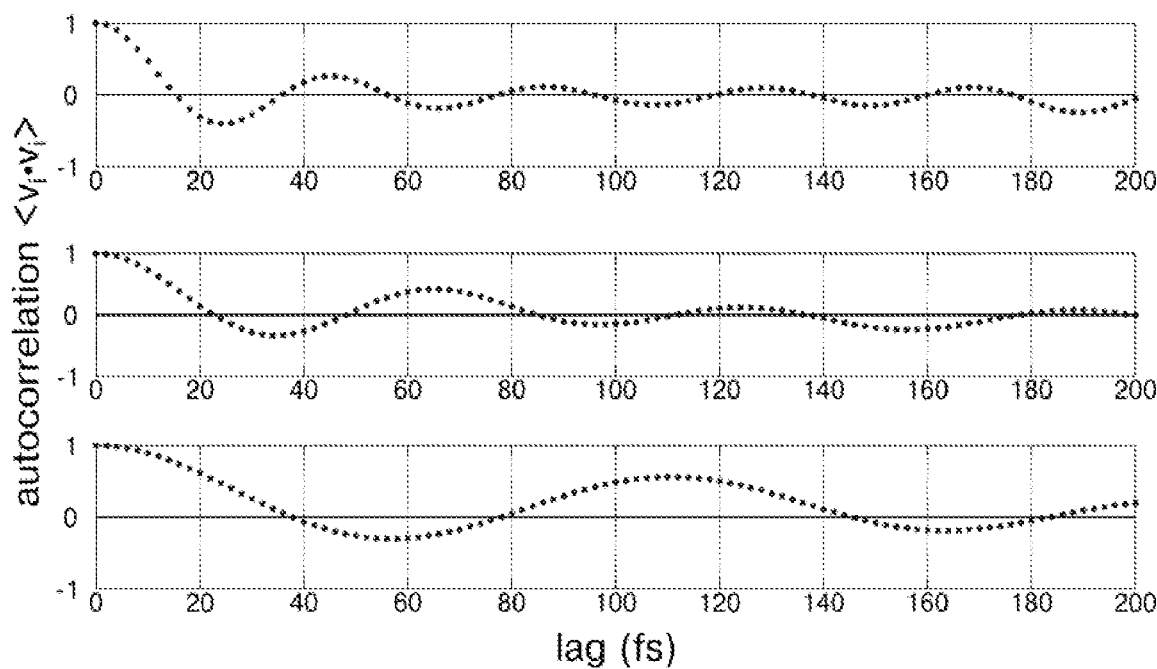
FIG. 22 shows velocity autocorrelation function in three CNTs.

The strength of inter-particle interaction between substance particles is, to a first approximation, represented by the coefficient of a linear approximation to the force versus distance relationship, or spring constant k. In some embodiments k is estimated from the nearest neighbor U relationship. In some embodiments, the coefficient is estimated from a combination of U interaction plus coulomb interactions. In some embodiments coulomb interactions can be estimated with point charges, dipoles, or other suitable multipoles. In some preferred embodiments the force versus distance relationship is obtained from MD simulations at the approximate expected operating pressures and temperatures. In other preferred embodiments, k is obtained from velocity or position correlation data, such as the velocity autocorrelation function which can be related to the speed of sound, and thus the spring constant. FIG. 22 shows the velocity auto-correlation function as computed from the axial velocities $v\_z$ of the water molecules, normalized so that the correlation is 1 at zero time lag. For a given number of substance particles, a narrower channel forces the substance particles into closer proximity. This tight packing increases the effective spring constant, which is visible as an increase in the frequency of oscillations.

In cases where a linear spring constant is insufficient to model the interaction between substance particles, a nonlinear model may be used, such as the Toda potential.

Nanojump Width

Nanojump width is an important consideration of the optimization procedures. Nanojump width relates to the following effects: the barrier to initiate motion; the temperature range for nanojumps stability; nanojump mass; nanojump speed; phonon damping; nanojump interactions with other nanojumps; among others. For example, one approximate expression for the nanojump width is $a^2*(k/(4h))^{(1/2)}$, where a is the PES wavelength, h is the amplitude of the component of the PES with wavelength a, both figured along a particular trajectory, and k is the interaction strength between particles, also referred to as the inter-particle spring constant.

In some embodiments, nanojump width is measured using numerical simulation. Nanojump width can be more easily estimated when nanojumps are sparse, in other words, when they are spaced apart by a distance at least equal to their width. In one embodiment, substance particles are placed in the nanochannel with close to one particle at every nanochannel wavelength, one particle every two wavelengths, or in general one particle every n wavelengths, where n is an integer, forming a ratio 1:n. Choice of particle density should correspond to that value nearest expected substance density at conditions which will be used in the application at hand. For example, if prior simulations were conducted at a range of contained particle densities, such simulations can be used to estimate the ratio of 1:n closest to the relevant particle densities for application. In one embodiment, the deviation from exact correspondence to 1:n spacing should be equal to one substance particle, either added or removed. As specified described herein and known to those in the art, this corresponds to $|S|=1$.

To facilitate the measurement of nanojump width, MD simulations can be conducted at temperatures such that $k\_B T \sim < E\_PN$. In a preferred embodiment, the system is initialized at room temperature and then equilibrated. If operating temperatures are different from room temperature, the temperature of the system can be gradually raised or lowered to such temperature. Positional data for substance particles are post processed using standard numerical techniques and methods disclosed herein. For example, particle positional coordinates measured down the axis of the nanochannel are not conducive to observing nanojumps. Instead, the particle positions measured down the axis are converted such that each particles displacement is measured from the respective minimum that the particle would occupy given S=0, and are generally labeled $u\_i$.

Novel methods are disclosed herein for the identification and characterization of nanojumps. When simulation results are plotted of the displacement $z\_i$ of the water molecules i, i=1, ..., N, relative to a single origin, nanojumps can not be perceived in the data, see the top row of panels in FIG. 20, in which $z\_i$ is plotted versus the index of the water molecules for, left to right, (4,4), (5,5) and (6,6) nanotubes.

Figure 20:
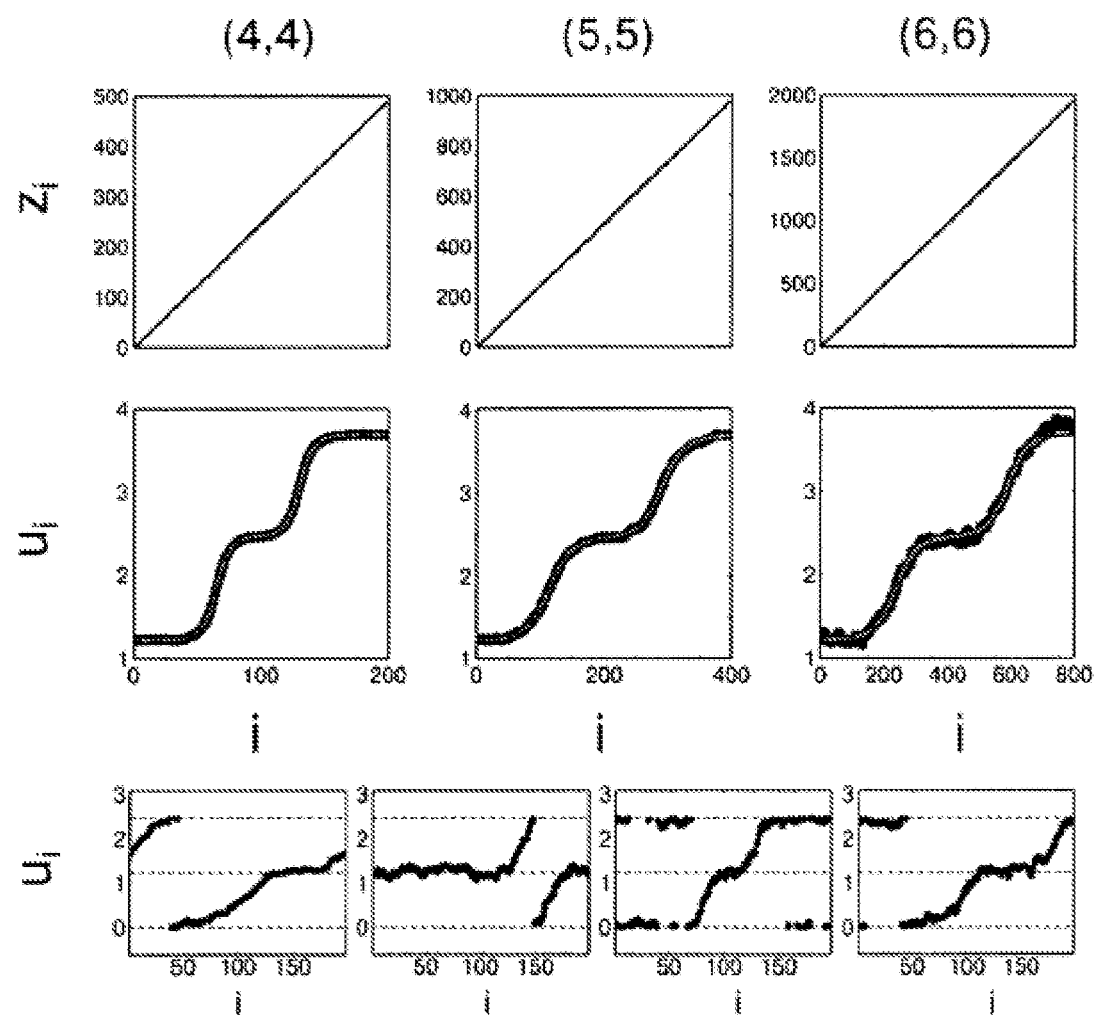
FIG. 20 shows a technique of plotting nanojumps with u_i in three CNTs.

Plotting the displacement $u\_i$ of each water molecule relative to its own origin, as described herein, and possibly using other methods described herein, reveals the nanojumps, as shown in the middle row of FIG. 20, for left to right, (4,4), (5,5) and (6,6) nanotubes. Data processing includes using a triplicate system, as described herein, and healing of the modulo function, where $u\_i'=mod(z\_i)$, and $u\_i'$ can be used to obtain $u\_i$ after further post-processing. Fitting molecular simulation data of the displacement $u\_i$ to theoretical predictions, such as from the FK model, is done using a trust-region nonlinear minimization algorithm (which performed better than the Levenberg-Marquardt algorithm) of the error between the curve fit and the data. A few error metrics were trialed including least-squares. The LAR method (absolute value of error) is considered less sensitive to outliers and appeared to give slightly better reliability. Note that when a nanojump spans the system boundary, difficulties arise unless periodic images of the system are included. Nanojumps are fit to a triplicate system, that is, the system is replicated once to the right of the system ([lambda, 2lambda]) and once to the left ([-lambda, 0]), where lambda is wavelength of the nanotube potential. The error function is defined only for the span [0, lambda]. In the middle row of panels in FIG. 20, the fit shows agreement between FK prediction and the numerical simulation data, as the line showing the arctan FK prediction is barely visible as it fits within the width of the points showing the simulation data points. The fitting procedure returns the nanojumps width and the position of the nanojumps. The algorithm can handle systems with multiple nanojumps that are not too crowded. For nanojumps whose velocity is not too high, the nanojumps can be tracked in time. Problems arise when nanojumps may sometimes reverse direction and nanojumps sometimes move large distances, since it can not be determined when using PBCs if a nanojump traveled rightward or leftward to the new location. In particular, the maximal distance the nanojump moves in an interval must be less than half the average nanojump-nanojump spacing. If there is only one nanojump, it must always move less than half the system length in each interval in order to track the nanojump in time.

To obtain $u\_i$, lab-frame center-of-mass (COM) of each water molecule (x, y, z)\_(i, COM) are first calculated. The COM z-coordinate $z\_(i, COM)$ can be used. The displacement $u\_i=mod(z\_(i, COM), lambda)$ is computed. However, the raw function $u\_i$ must be postprocessed. First, when a sequence of water molecules is near the bottoms of potential wells, some will be located just to the left of the minima ($u\_i$ approximately lambda), and some just to the right of the minima ($u\_i$ approximately 0). Thus, the function $u\_i$ will contain frequent and random switching between approximately lambda and approximately 0. See the lower row of FIG. 20 for examples of such artifacts in the data, where the ordinate shows the displacement, prior to post-processing, and i is the index of the water molecules. Such switching is removed with a heuristic algorithm that searches for discontinuous-enough jumps in $u\_i$ and adds or subtracts lambda.

In one embodiment, nanojump width is visually estimated from post-processed data, for example using the full-width at half-maximum of the particle. In a preferred embodiment, post processed data is fit to a theoretical shape of the FK model, using standard numerical techniques or techniques described herein, from which nanojump width is obtained.

Figure 21:
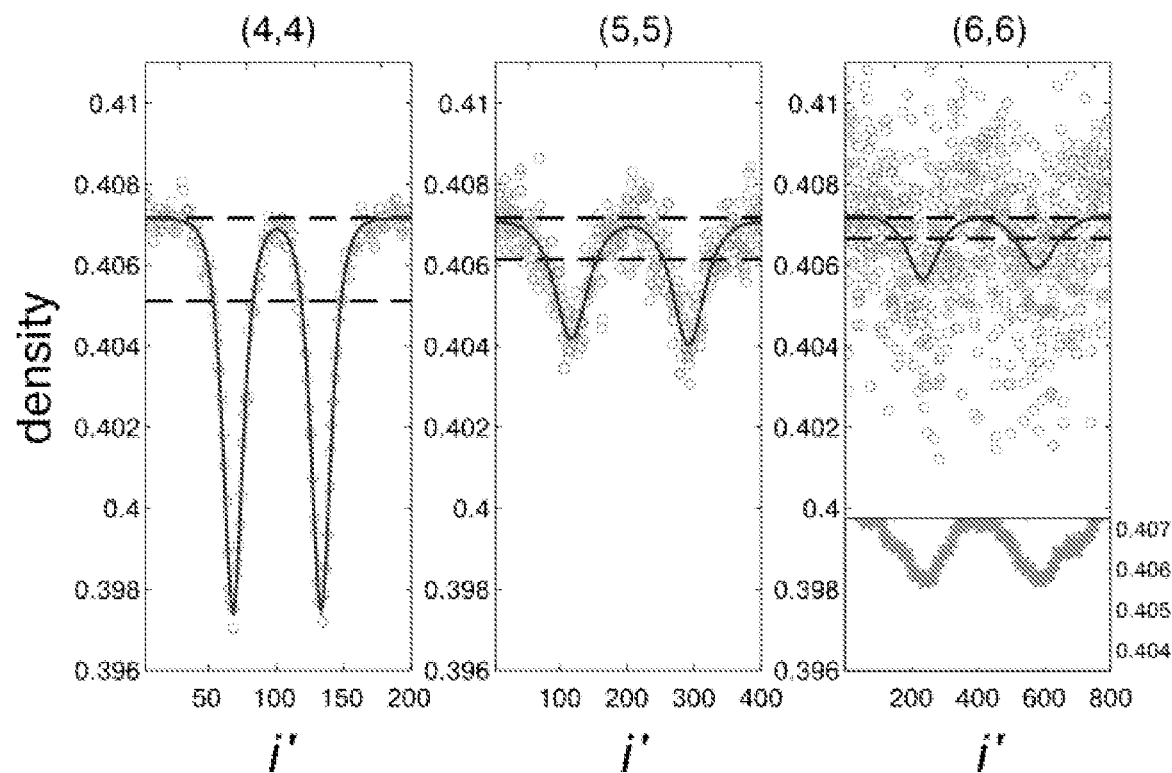
FIG. 21 shows water density in three CNTs and nanojumps amid thermal noise.

In many cases thermal noise can make it difficult to observe nanojumps. However, a numerical fit to MD data can still find nanojumps. For example, in FIG. 21, each data point from numerical simulation, shown as an open circle, is the density in the neighborhood of the water molecule labeled with the index i' along the nanotube. The density is given in number of water molecules per angstrom. The figure shows results, from left to right, for the (4,4), (5,5), and (6,6) carbon nanotube. For the (4,4) and (5,5) nanotubes, two nanojumps are clearly visible. The data is well fit by the hyperbolic secant profiles predicted by the FK model. For the (6,6) nanotube, the nanojumps are not apparent in the data points due to its large scatter. However, the data is still fit by two hyperbolic secants. The lower axes for the (6,6) nanotube shows the same data as the upper axes after applying a Savitzky-Golay smoothing filter of width 125. The nanojumps are clearly visible in the processed data and compare well with the hyperbolic second fit to the data.

In cases where more significant thermal noise is present, nanojumps may still be difficult to observe in MD data. In those cases time-averaging or spatial-averaging can still be used in order to "smooth out" the stochastic fluctuations of thermal noise. The width of the spatial averaging window may be approximately the expected width of the nanojumps. The length of the time averaging window should be long enough to smooth thermal fluctuations but short enough that the nanojump does not diffuse a significant distance.

Figure 25:
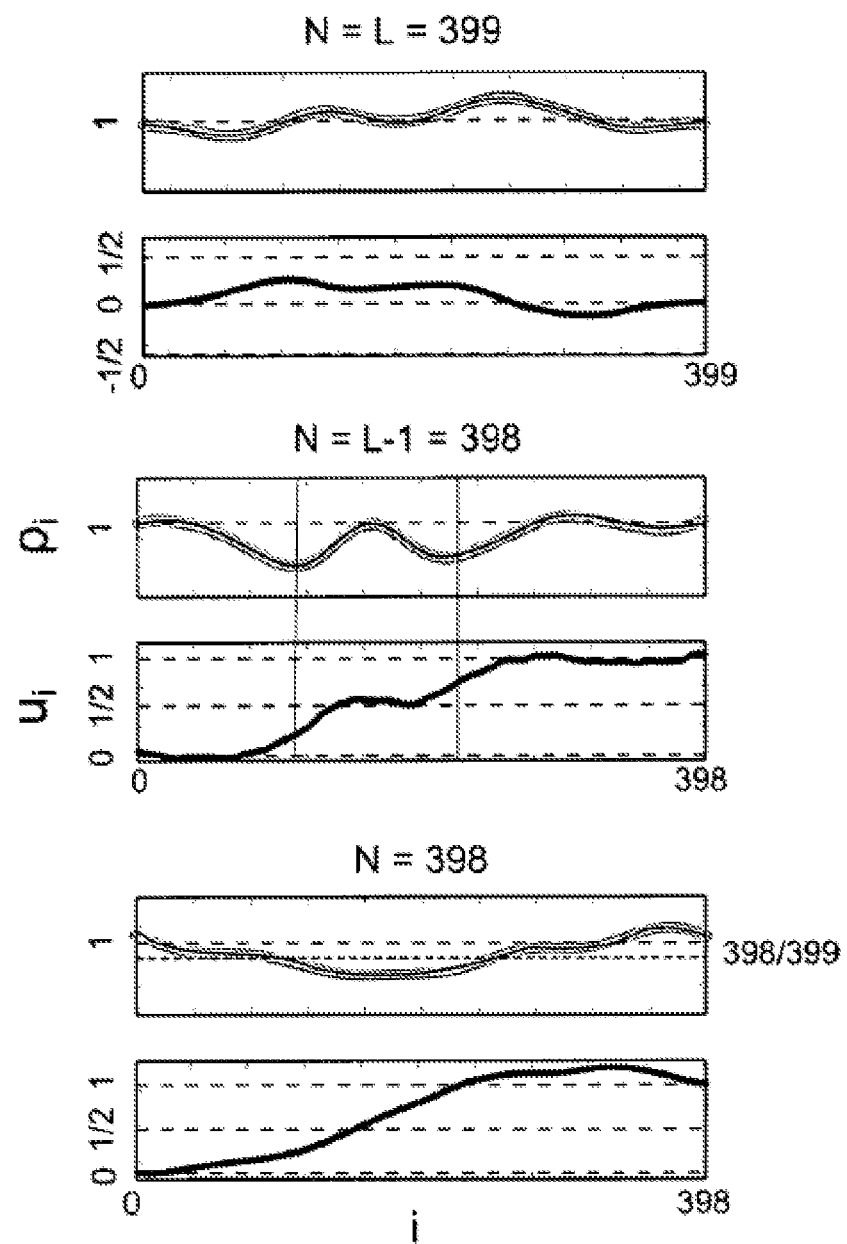
FIG. 25 shows numerical data from (5, 5) carbon nanotubes at 300 K visualizing nanojumps even at high thermal noise.

Shown in FIG. 25 are numerical data from (5, 5) carbon nanotubes at 300 K. The data points overlap and appear as a continuous curve. The top row of panels shows the local density centered at each water molecule i, after smoothing with a second-order Savitsky-Golay filter centered at the position of each water molecule, with a width of 15 water molecules. The bottom row of panels shows the displacements of the N water molecules, $i=1, \ldots, N$, as in FIG. 4. In the two left-most panels, $N=L=399$, and so $S=0$ and no nanojumps are present. The density data is fit to the first three phonon modes, shown as a line that falls within the thickness of the data curve from the numerical results. The right-most two panels are from a nanotube whose potential was smoothed in the manner described for FIG. 4. There are no nanojumps present. The density data is fit to the first three phonon modes, shown as a line that falls within the thickness of the data curve from the numerical results. The central two panels are for a case for which $N=L-1=398$, so $S=-1$, and there are two nanojumps. The density data is fit to the hyperbolic secant profile as determined from the theory of solitons, plus the first three phonon modes, and shown as a line that falls within the thickness of the data curves from the numerical results. Even when the thermal energy $k\_B\ T$, where T is temperature and $k\_B$ is Boltzmann's constant, is of the order of 100 times the amplitude of the substrate potential, nanojumps can still be readily discerned using the techniques disclosed herein.

In some cases, especially those directed toward continuous, fast flows, nanojacks are designed with closely spaced nanojumps. Therefore a method is used to obtain nanojump width when far from $|S|=1$. In a simulation, particles are loaded into a nanochannel near expected operating conditions. As previously mentioned herein, initial temperatures during equilibration are, in one embodiment, preferred to be near room temperature. In one embodiment temperatures are lowered to temperatures near $k\_B\ T\sim<E\_PN$. In a preferred embodiment temperatures are lowered to a very low temperature near $k\_B\ T\sim0$. The hull function method can be used to visualize closely spaced nanojumps.

Figure 18:
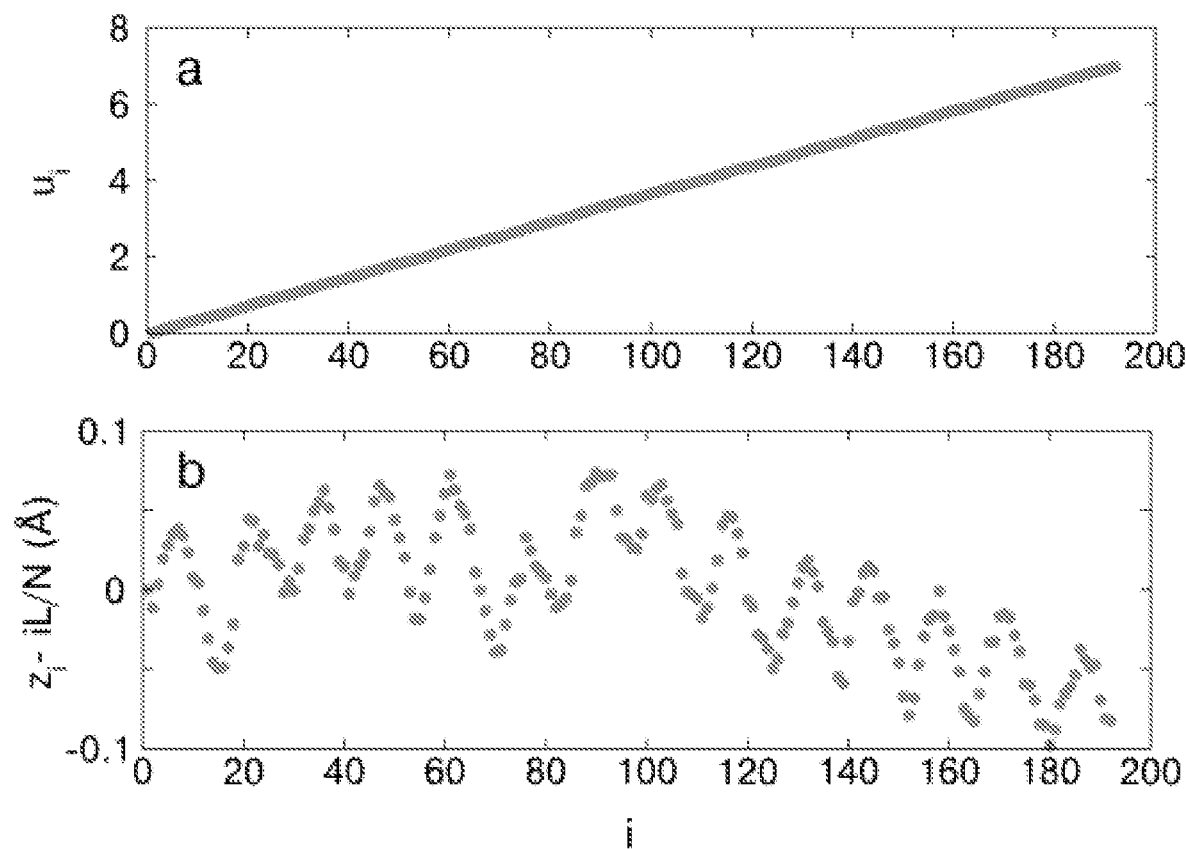
FIG. 18 shows displacement of water molecules in a (4,4) CNT and visualizes nanojumps when they are close together.

For example, when the separation distance between nanojumps is comparable to the nanojump width then adjacent nanojumps may overlap. Discerning the individual nanojumps may then be difficult. In FIG. 18 panel (a) is shown the displacement of water molecules in a (4,4) carbon nanotube at 5 K for which $L=199$ and $S=-7$, so there are 14 nanojumps. The nanojumps width is approximately 6.8 water molecules, approximately one half of the distance between adjacent nanojumps. It appears from FIG. 18 panel (a) that there are no nanojumps. However, after using our novel method, based on the hull function, each of the 14 nanojumps is apparent in FIG. 18 panel (b). In this method, the total displacement x_i of any particle i, $i=1, \ldots, N$, is written as the hull function, $x\_i=C+iL/N+H(C+iL/N)$, where C is a constant and L/N is the spacing between particles, assuming constant spacing. Using the hull function, the displacement x_i, is replaced by $x\_i-(C+iL/N)$, that is, the constant increase in displacement is subtracted, leaving only the variation from uniform placement, which, as seen in the figure, can be swamped by the accumulated displacement. The data shown in FIG. 18 panel (a), after such a subtraction, is shown in FIG. 18 panel (b), now revealing the nanojumps. This technique is critical in designing nanojacks for many applications, for example, in determining how flow rate depends on number of nanojacks, and how overlap between nanojumps affects discrete metering of the contained substance Simple Estimation Procedures In some embodiments, especially those for discrete metering, the discrete protocol can be used. For example, an armchair nanochannel is selected whose interior potential wavelength is close to the average expected distance between contained particles. This produces widely spaced nanojumps. Furthermore, the operating conditions can be selected to enhance or optimize performance. For example, low temperatures can be chosen. Low temperatures are conducive to steady nanojump motion. In some embodiments, temperature is considered low when as low as possible but still above the temperature based on the energy scale of nanojump motion, E_PN or nanojump creation energy, whichever is lower. Absolute pressures can be used to compress or expand contained substance, so that contained particle spacing more closely matches with an integer multiple of the nanochannel interior potential wavelength, and nanojumps become widely spaced. An estimate of compressibility of the contained substance can be used to estimate needed pressures, or MD simulations can be used. In some cases, substance particles can be chemically modified, increasing or decreasing the force of repulsion or attraction between neighboring particles. In other cases chemical modifications can be made to the wall of the nanochannel, changing the interior potential, or PES.

Two distinct methods for nanojack design are disclosed, one tailored to fast, continuous flow (the "continuous protocol") and one tailored to discrete, finely controlled flow (the "discrete protocol").

In some embodiments, especially those for continuous flow, a continuous protocol can be used. The continuous protocols can pursue goals that in some cases or in some regard contrast with those of discrete metering. In the continuous protocol, the optimization can be applied to find systems for which flow occurs at the lowest level of forcing or energy input. Consequently, in some embodiments those nanochannels whose interior potential wavelength or wavelength multiple is maximally irrational compared with the expected mean spacing between contained particles are used. In the continuous protocol, low temperatures can be used in order to maximize flow speed. However, in some embodiments higher temperatures can lead to faster flow at very low applied forcing, where the applied forcing F_applied about f_PN. Other device or system choices and choices for operating conditions can be made as well.

It should be recalled that the potential energy in the nanojack depends on the substance particle position in three-dimensional space. The "interior potential lambda" refers to the most appropriate lambda as it affects the contained substance. For example, if the contained substance substantially moves along paths parallel to the nanojack axis, then the lambda will, in general, be different than if the dominant paths are, for example, helical spirals. In some cases, changes to the operating conditions with the same nanojack can change the dominant paths and so change the nanojack performance.

In some embodiments nanojump width can be determined from estimates of the inter-particle interaction between substance particles together with estimates of the amplitude and wavelength of interior nanochannel potential. Details of the equations relating these quantities to nanojump width are outlined herein or known to those skilled in the art. In general, wider nanojumps decrease flow resistance.

Nanojump Motion

Nanojump speed and its relationship to applied forcing, and thus predicted mass transport rates, can be estimated with MD simulations or estimated from FK model theory. For example, at high forcing, f, the velocity of a nanojump, V, can be estimated by the FK model, for example $V = 1/\sqrt{(1 \pm (4*n/pi/f)^2)}$ where n represents a velocity proportional damping constant.

The level of forcing to achieve desired flow rates can be estimated. For pressure-driven flow, the forcings can be obtained from standard MD simulations or predicted from FK model theory. For flow driven by electrical current, applied forcing can be estimated from quantum simulations performed by those suitably skilled in the art, or from physical experiments. For flow driven by other means, such as impulses of pressure, or sound wave propagation along the nanochannel length, or through drag by motion of molecules exterior to the nanochannel, amplitude of applied forces can be estimated by molecular dynamics simulations or quantum simulations.

In a preferred embodiment, nanojump speed under forcing is obtained from MD simulation. In many cases driving forces can be assumed to be divided equally to all particles. In some embodiments, flow rates can be measured as a function of applied forcing. In preferred embodiments, nanojump trajectories are tracked in time. For example, at selected intervals from the output of an MD simulation, nanojumps are located using the nanojump fitting methodology described herein, and nanojump position versus time is plotted. Problems can arise when nanojumps may sometimes reverse direction or nanojumps sometimes move large distances since it can not be determined if a nanojump traveled rightward or leftward to the new location. In general, the maximal distance the nanojump moves in an interval must be less than half the average nanojump-nanojump spacing.

Figure 16:
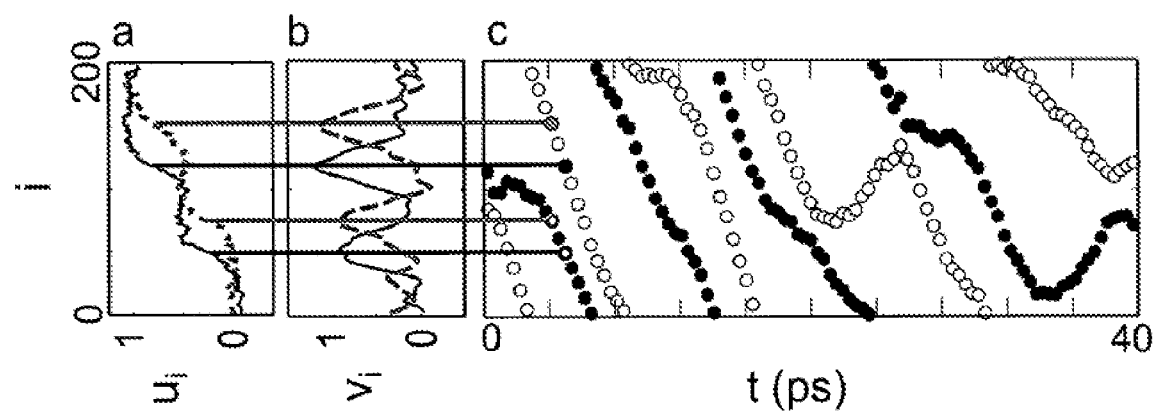
FIG. 16 shows nanojump position and velocity determination and plots nanojump position versus time in the (4,4) CNT.

FIG. 16 panel (a) illustrates nanojump tracking, where displacement u_i of water molecules from their earlier position is shown by the lighter line, and at 0.8 ps later in time is shown by the heavier line. The velocity v_i of the water molecules within the nanojumps is positive, while outside of the nanojumps the velocity is approximately zero, as shown in FIG. 16 panel (b). Horizontal lines are provided to help line up the nanojumps appearing in panel (a) with regions of positive velocity in panel (b), and show how the positions at the time of panel (a) correspond with positions in panel (c). Nanojump locations as a function of time are shown in FIG. 16 panel (c). One nanojump is indicated by open circles, and the other nanojump is indicated by closed circles. The slope of these nanojump trajectories is used to obtain the nanojump velocities. Sometimes nanojumps reverse direction, as seen by the open circles near 21 ps and again near 25 ps. Data is from (4,4) carbon nanotubes at 300 K with S=−1, where each water molecules is forced with f=0.4 pN.

Figure 15:
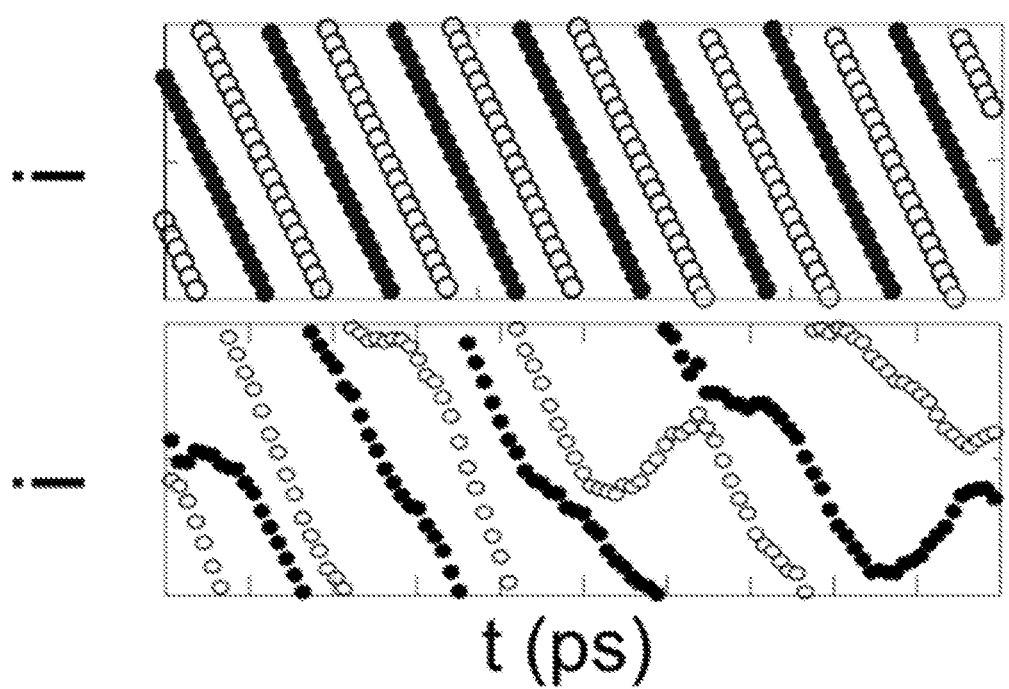
FIG. 15 shows nanojump trajectories at both low and high temperatures in the (4,4) CNT.

When a larger forcing is applied to the water molecules, or a lower temperature, the nanojump locations as a function of time appear as straighter trajectories, indicating nearly constant velocity as a function of time, as shown in the upper panel of FIG. 15, relative to the trajectories at lower forcing and higher temperature, shown in the lower panel, reproduced from FIG. 16 panel (c). Data from the (4,4) carbon nanotubes with S=−1. Upper panel at 5 K and where each water molecule has an applied force of 0.8 pN, compared with lower panel at 300 K, with a forcing of f=0.4 pN.

By determining nanojump behavior versus applied forcing and temperature, the discrete nature of flow can be appreciated and novel means of controlling flow can be employed. In a preferred embodiment simulations are run at a variety of temperatures including very cold temperatures, in order to check that nanojumps do not become pinned or stuck, due to a lack of thermal energy.

Figure 24:
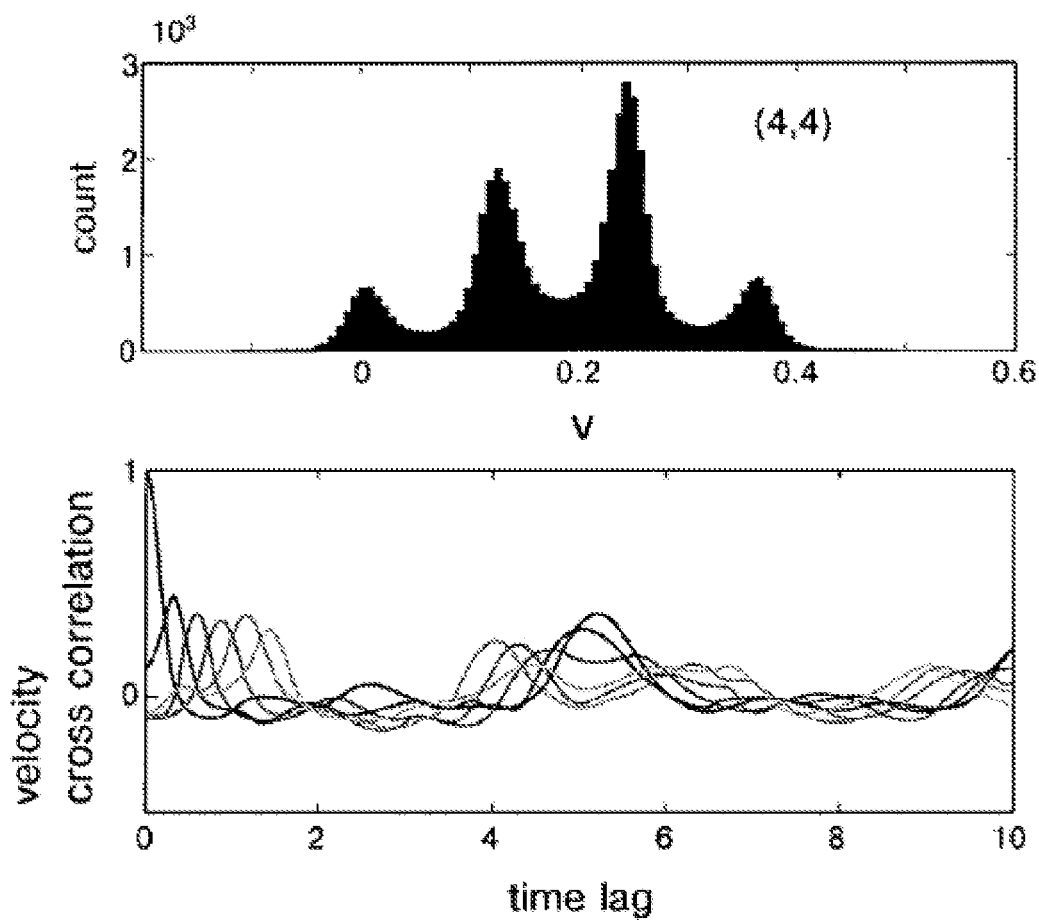
FIG. 24 depicts alternate methods to measure nanojump speed.

Other numerical techniques can also be used to measure nanojump speed. For example, the velocity cross-correlation (VCC) function between neighboring or distant substance particles can be used to detect nanojump speed. A peak in the VCC between particles I and J at a time lag of t_lag shows that nanojumps transit the distance between the two particles in a time span of t_lag. In another technique, the velocity of each substance particle can be time-averaged with a window of length t_win, where t_win is approximately equal to the time for at least two nanojumps to pass the particle. When nanojump motion is particularly stochastic, this method will show a multi-peaked histogram corresponding to 0, 1, 2, etc. nanojumps passing the particle. These techniques are shown in FIG. 24.

Nanojumps experience a barrier to motion known as the Peierls Nabarro barrier, which is discussed herein and known to those skilled in the art. When designing methods of driving flow, the driving force applied to the particles must be sufficient to overcome this force barrier, f_PN.

Figure 17:
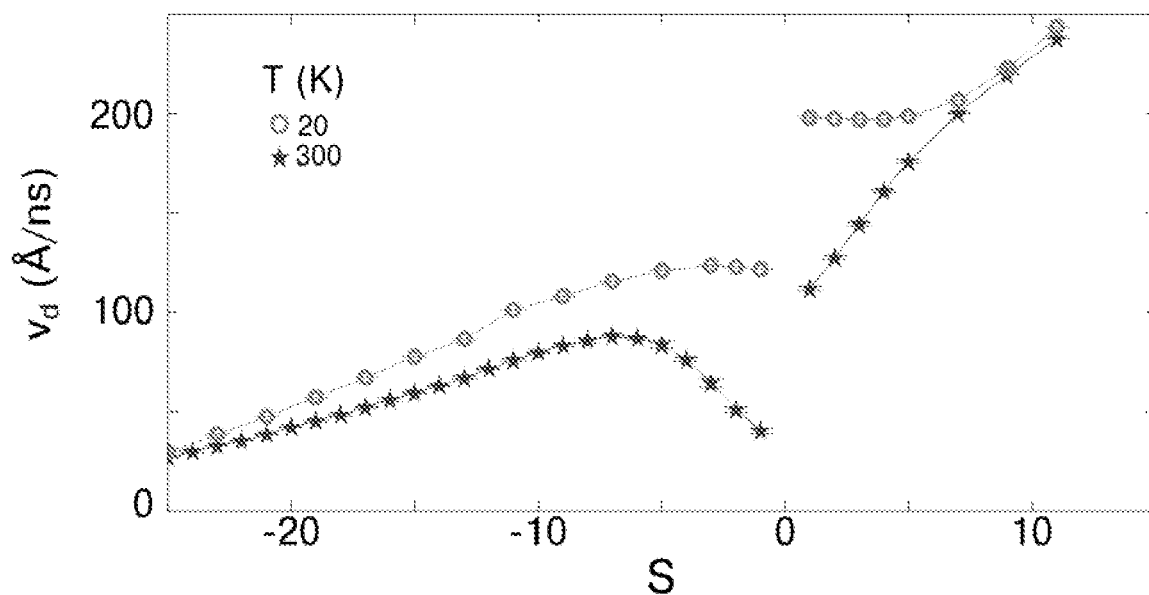
FIG. 17 shows the nanojump velocity v_d versus the parameter S in the (4,4) CNT.

FIG. 17 shows the nanojump velocity v_d versus the parameter S in the (4,4) CNT. There is an asymmetry in the nanojump speed shown in the figure, where compressive nanojumps are shown to move faster than expansion nanojumps. The asymmetry is predicted by the FK model including nonlinear interparticle interactions.

Operating conditions can be adjusted in order to affect nanochannel filling. Absolute pressures or temperatures can be changed. In some cases, chemical moieties can be attached to nanochannel exteriors in order to enhance or hinder filling. Additionally, electric fields applied to the nanochannel walls can attract or repel substance particles and thereby affect nanochannel filling.

Applications may be constrained by economics. Some nanojack designs may be more cost effective than others over particular extents in time. Such considerations can be included in the methods.

Preferred Methods for Discrete Metering

Molecules can be metered singly or in small groups. For molecules that are in the form of a long chain, the method and system displaces the chain by an atomic-scale amount. Molecules are displaced by a distance determined, in part, by the geometry of the nanochannel. For example, in some carbon nanotubes, the distance by which molecules are displaced is related to the spacing of carbon atoms. In many embodiments, the displacement is related to the wavelength of the PES. The methods and systems of the invention can be used to control and deliver substances that in bulk would be liquid, or of substances that in bulk are found to be solid. The types of substances can be inorganic materials, for example, gold or water, or organic materials, for example, amino acids, nucleotides, or polymers of amino acids or nucleotides.

In some preferred embodiments for discrete metering of substance, the nanojumps are widely spaced. The passage of each widely spaced nanojump transports one or a few molecules, causing the transport to be metered by the number of nanojumps transiting the nanojack. Since the number of nanojumps can be controlled, the amount of substance output from the outlet of the channel or distance moved as a function of time can be controlled. In this way, the number of exiting molecules can be counted out or controlled in order to facilitate being detected. In some preferred embodiments, the metering of the number of molecules does not require that the mechanism driving the molecules through the nanochannel be switched on and off for each molecule to be transported. Rather, in these embodiments, the passage of the nanojumps at known spacing provides metering. The periodic passage of nanojumps transports molecules to the end of the nanochannel with a particular frequency. For instance, a constant current can be applied to the nanochannel wall to provide a constant forcing.

These methods meter single molecules, or a group of atoms or molecules, or a discrete length of molecule delivered from the nanojack as a function of time.

The outlet of the nanojack can be moved relative to a substrate to deposit a controlled amount of the substance on specific locations on the substrate. Alternatively, the substrate can be moved. The outlet of the nanojack may be in a solution where the exiting contained substance reacts, combines, or interacts with substances in solution, which may be present having been delivered from other nanojacks.

Some molecules in biological cells are in the form of a long strand, for example, as a polymer, made up of smaller parts linked together. DNA is one such molecule. There is great interest in sequencing strands of genetic material. The genetic information of DNA is composed of a sequence of nucleotide molecules known by their single-letter abbreviations G (guanine), T (thymine), A (adenine), and C (cytosine) (and in the case of RNA, U (uracil)). Sequencing DNA consists in determining the particular order in which these G, T, A, and C nucleotides are arranged on the DNA strand. Proteins are another type of polymer. Proteins are composed of amino acids linked together. There are over 20 different types of amino acids used to construct the thousands of different proteins—including at least alanine (ala), arginine (arg), asparagine (asn), aspartic acid (asp), cysteine (cys), glutamic acid (glu), glutamine (gln), glycine (gly), histidine (his), isoleucine (ile), leucine (leu), lysine (lys), methionine (met), phenylalanine (phe), proline (pro), serine (ser), threonine (thr), tryptophan (trp), tyrosine (tyr), and valine (val). In addition to the 20 amino acids listed here, there are others that are naturally occurring and others that are man-made. Any of these may be made part of a protein. Proteins differ, in part, due to their amino acid sequence. There is great interest in developing techniques to determine the sequence of the components making up nucleic acids, such as DNA, and proteins, and to do this accurately, quickly and inexpensively. In some techniques, the polymer is advanced through or past a sensor. The disclosed compositions, methods and systems can control the motion of these molecules as part of a device to determine the sequence. There are other polymers, other than DNA and proteins, for which the device can be used to help determine their sequence. A component of such devices may be a detector. The detector may be, for example, a photodetector or an electrical circuit. The detector may detect electrical perturbations arising from the contained substance. The circuit may include the nanojack or a part thereof, or may include part of the surroundings near the nanojack, or some combination of the nanojack and surroundings. There is also interest in constructing nucleic acids and proteins from their component nucleotides and amino acids, respectively. For example, in one particular example, four nanochannels, one each for G, T, A, and C, can be used in the proper order to deliver nucleotides to be linked together in a desired nucleic acid sequence. In another example, four nanochannels, one each for G, U, A, and C, can be used in the proper order to deliver nucleotides to be linked together in a desired nucleic acid sequence. There are also other polymers, both organic and inorganic, for which systems can be used to construct desired sequences.

In some embodiments, the disclosed compositions, methods and systems can discriminate the difference between the monomers or components of a polymer and consequently determine the sequence of the polymer.

An advantage of certain implementations of the present embodiment is that design, fabrication and operation of the nanochannels can be done such that the amount by which the molecules of the substance advance can be determined. This discrete advance can be utilized as part of a system. For instance, the discrete advance can be coupled to other objects, either through the walls of the nanochannel or through the nanojack ends, and utilized to advance these objects, such as to ensure atomic-scale or nano-scale positioning of objects, such as for nanomanipulators or laser systems.

In certain embodiments, materials can be discretely metered without the need to heat them. On the contrary, atomic scale control can be enhanced as temperature is decreased. And certain embodiments can provide motion and control of uncharged molecules.

Figure 13:
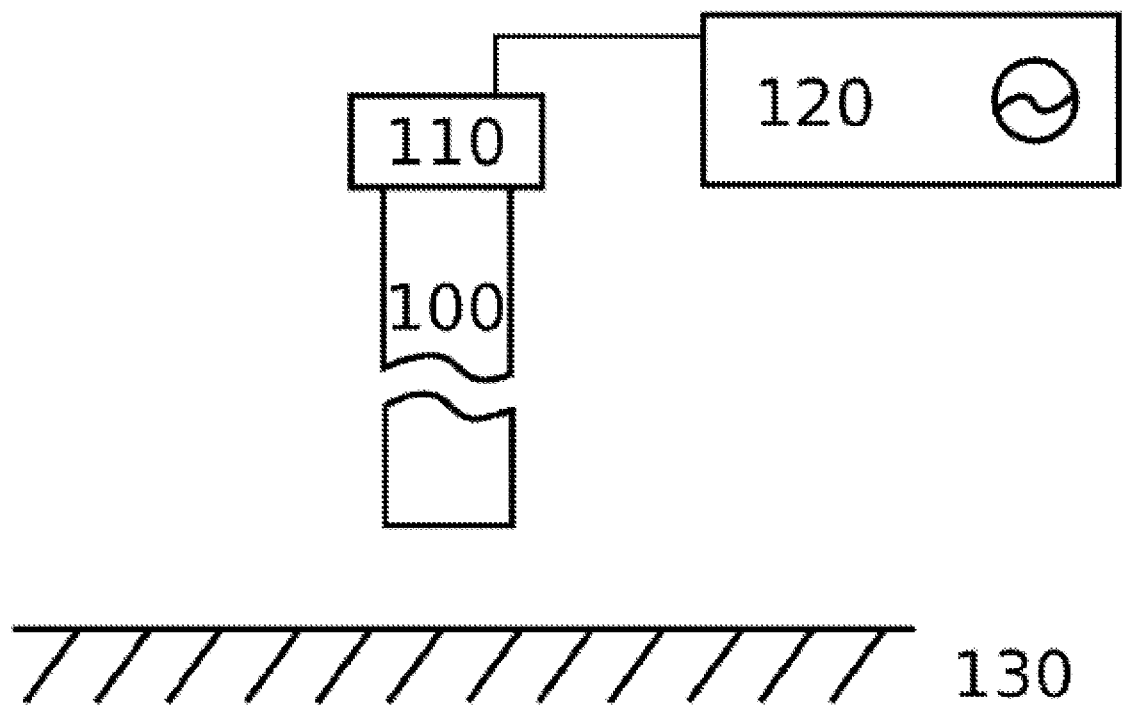
FIG. 13 is a schematic of one embodiment for a device for delivering molecules in a controlled manner. Only a single nanochannel is shown. An actual device can have one or more nanochannels. The nanochannel 100 is connected by a coupling 110 to a mechanism or device labeled 120. Device 120 can deliver a mechanical or electronic forcing to the nanochannel 100. The coupling can be at one or both ends of the nanochannel, or can be along the length of the nanochannel, or can be along part of the length of the nanochannel. The ejected molecule(s) can be delivered onto a surface 130.

FIG. 13 is a schematic of one manifestation for a system for delivering molecules in a controlled manner. Only a single nanochannel is shown. An actual device can have one or more nanochannels. The nanochannel 100 is connected to a coupling 110 to a mechanism or device labeled 120. Device 120 can deliver a mechanical or electronic forcing to the nanochannel 100. The coupling can be at one or both ends of the nanochannel, or can be along the length of the nanochannel, or can be along part of the length of the nanochannel. The ejected molecule or molecules can be delivered onto a surface 130. Thus, the system of the embodiments is comprised of a nanojack or nanojacks component and a device to cause the substance to move through the nanochannel.

There is interest in isolating individual chemical reactions within nanodroplets or nanoscale reaction vessels. In some embodiments, nanojacks discretely meter atoms or molecules into nanodroplets or nanoscale reaction vessels.

Methods and Applications for Stationary Nanojumps

In one aspect, nanojumps can be useful by the field they create. For example, the inhomogeneous distribution of contained particles can be useful in and of itself. In another aspect, the precise and controllable distribution of particles by creating a nanojump, such as by an applied pressure, can be utilized to affect the motion of nearby particles, including molecules, atoms, electrons, or photons. Creating or destroying nanojumps alters this field.

In another aspect, the increase or decrease of spacing between the particles in the nanojump can be useful for altering the flow of electrons in the channel walls or through the substance itself. For example, if the substance is a metal, then by creating expansion nanojumps, the resistivity of the contained metal can be increased.

In another aspect, nanojacks can be used to store information, where the presence or absence of a stored nanojump may constitute a stored bit. Such memory devices may be coupled to photon emitters and detectors and computing devices. Nanojacks in particular arrangements may also serve as the basis for logic gates.

Nanojumps can be excited by interaction with optical systems, permitting a novel type of optical circuitry. For example, nanojacks can be used to generate what is known by those in the art as slow light. The group velocity of light can be reduced by its propagation through a material in which the refractive index increases as the wavelength of light decreases. This implies, as known by those in the art, a negative dispersion. As nanojumps of the same type, for example, with a greater density than the intervening regions, will repel one another, nanojumps tend to be equally spaced. Operating conditions, nanochannel type and the contained substance can be chosen such that the spacing is appropriate for interacting with light of a certain wavelength. The periodic constructive or destructive interference along the length of the nanojack will result in a slowing of the light near a particular frequency. Another significant advantage of generating slow light with nanojacks is that the frequency at which they yield slow light can be tuned. The regular spacing between nanojumps can be varied by changing, for example, the operating conditions. For example, for fixed nanochannel and contained substance, the absolute pressure can be increased, resulting in more closely spaced nanojumps. Presently, nearly all systems for generating slow light are designed to work at a single frequency or the facility to change the operating frequency is expensive. Nanojack devices have the great advantage of being tunable. Furthermore, nanojacks exist at extremely low temperatures. At low temperatures, thermal fluctuations are reduced, and so the spacing between nanojumps fluctuates less than at higher temperatures. In this way, the interaction between the nanojack and light is more effective.

EXAMPLE

The following modeling techniques are provided as exemplary, novel methods. The new compositions of matter described herein may be modeled to evaluate properties of single-file flow in a nanochannel. Applying numerical methods of the FK model or Toda model reveal new and unexpected properties for single-file flow.

Instead of plotting particle positions along the channel axis as is customary, particle coordinates are plotted in terms of the variable $u\_i$, which is the axial coordinate relative to the minima the particle would be in when in the commensurate state. The variable $u\_i$ is fit to the functional form of the soliton from the FK model using a standard fitting procedure which allows (a) determination of nanojump width, (b) determination of nanojump position(s) within nanochannel(s), and (c) tracking of nanojumps over time.

The local particle density, rho, can be fit to an alternative form of the FK model soliton to find and measure nanojumps. At high temperatures, particle positions $u\_i$ or density rho can be smoothed with spatial and temporal averaging windows. The spatial averaging window should be short enough that the nanojump width or amplitude is not altered. The time window can be short enough such that the nanojumps are more likely to remain relatively stationary.

The hull function is used to plot particle positions, to find and track nanojumps when closely spaced. The cross correlation function of particle velocities is used as an additional way to measure nanojump speed, FIG. 24. Nanojump trajectory plots are used to measure nanojump speed. Time averages of particle velocities are used to measure nanojump speeds, FIG. 24.

The Toda potential is applied to cases where the substance particle interaction is significantly nonlinear. Parameters of the Toda model are obtained from MD data. A combined Toda-FK model is used to predict nanojump velocity.

In MD, the atoms of the nanochannel wall are replaced with a potential grid to speed up simulations. The accuracy of PME is turned off or substantially reduced to speed up simulations. Long MD cutoffs are used for greater accuracy while preserving efficiency. In MD, the Lowe-Andersen or other Galilean invariant thermostat is used for single-file flows. Low temperatures are used to more easily find and track nanojumps. MD data is output frequently to better track nanojump trajectories.

The minimum force required to achieve flow is determined and flow rates are predicted by determining FK model parameters h and k.

REFERENCES

All patents, patent applications, patent application publications and other publications that are cited herein are hereby incorporated by reference as if set forth in their entirety to the extent that the incorporated references are not inconsistent with the present disclosure or otherwise narrow the claimed subject matter supported by the present disclosure. To the extent that portions of the incorporated references are inconsistent with the present disclosure or otherwise narrow the claimed subject matter supported by the present disclosure, those portions are expressly excluded from the present application.

The provisional application cited herein and exhibits thereto forms part of the specification of the application and is hereby incorporated by reference as if set forth in its entirety to the extent that the incorporated references are not inconsistent with the present disclosure or otherwise narrow the claimed subject matter supported by the present disclosure. To the extent that portions of the incorporated references are inconsistent with the present disclosure or otherwise narrow the claimed subject matter supported by the present disclosure, those portions are expressly excluded from the present application.

It should be understood that the methods, procedures, operations, composition, and systems illustrated in figures may be modified without departing from the spirit of the present disclosure. For example, these methods, procedures, operations, devices and systems may comprise more or fewer steps or components than appear herein, and these steps or components may be combined with one another, in part or in whole.

Furthermore, the present disclosure is not to be limited in terms of the particular embodiments described in this application, which are intended as illustrations of various embodiments. Many modifications and variations can be made without departing from its scope and spirit. Functionally equivalent methods and apparatuses within the scope of the disclosure, in addition to those enumerated herein, will be apparent to those skilled in the art from the foregoing descriptions.

What is claimed is:

1. A composition comprising a nanotube having a length and a substance contained within the nanotube, said substance comprising a plurality of substance particles arranged in a single-file fashion along the length of the nanotube,
wherein said substance particles are arranged to include at least one nanojump,
wherein said nanojump comprises a localized region within said nanotube wherein the average density of the substance particles within said nanojump differs from the average density of the substance particles in regions of similar size outside of said nanojump but within the same nanotube, and
wherein the substance particles in said regions of similar size outside of said nanojump but within the same nanotube are relatively stationary as substance particles within said nanojump region are transported along said nanotube by said nanojump.

2. The composition of claim 1 wherein the nanotube is a single-walled nanotube.

3. The composition of claim 1, wherein the nanotube is a multi-walled nanotube.

4. The composition of claim 1 wherein the substance contained within the nanotube comprises a plurality of water molecules.

5. The composition of claim 4 wherein said plurality of water molecules are below the bulk freezing temperature of water.

6. The composition of claim 1 wherein the substance contained within the nanotube comprises a plurality of amino acids.

7. The composition of claim 1 wherein the substance contained within the nanotube comprises a plurality of nucleotides.

8. The composition of claim 1 wherein said nanotube has an internal diameter that is between about 5.4 angstroms and about 10.2 angstroms.

9. The composition of claim 1 wherein the substance is a peptide.

10. The composition of claim 1 wherein the substance is a protein.

11. The composition of claim 1 wherein the substance is a polymer.

12. The composition of claim 1 wherein the substance is a DNA strand.

13. The composition of claim 1 wherein the substance is an RNA strand.

14. The composition of claim 1 consisting of 1 or 2 nanojumps.

15. The composition of claim 1 further comprising a device for applying a potential difference across the length of a nanotube.

16. The composition of claim 1 wherein the substance contained within the nanotube comprises a plurality of metal atoms.

17. The composition of claim 1 wherein the substance contained within the nanotube comprises a plurality of copper atoms.

18. The composition of claim 1 wherein the substance contained within the nanotube comprises a plurality of silicon atoms.

19. The composition of claim 1 wherein the substance contained within the nanotube comprises a plurality of gold atoms.

20. The composition of claim 1 wherein said substance particles are below the bulk freezing temperature of said substance under standard pressure.

21. The composition of claim 1 wherein said substance particles are below about 75K.

22. An array of nanotubes,
each nanotube having a length and each nanotube containing a substance within the nanotube,
said substance comprising a plurality of substance particles arranged in a single-file fashion along the length of the nanotube, and wherein said substance particles are arranged to include at least one nanojump,
wherein said nanojump comprises a localized region within said nanotube wherein the average density of the substance particles within said nanojump differs from the average density of the substance particles in regions of similar size outside of said nanojump but within the same nanotube,
wherein the substance particles in said regions of similar size outside of said nanojump but within the same nanotube are relatively stationary as substance particles within said nanojump region are transported along said nanotube by said nanojump.

23. The array of claim 22 wherein the substance contained in each nanotube is water.

24. The array of claim 22 wherein the array has a first end in fluid communication with a first reservoir comprising said substance.

25. The array of claim 22 wherein each nanotube has an internal diameter that is between about 5.4 angstroms and about 10.2 angstroms.

26. The array of claim 22 comprising two or more of:
a first nanotube containing a plurality of adenine nucleotides,
a second nanotube containing a plurality of cytosine nucleotides,
a third nanotube containing a plurality of guanine nucleotides,
a fourth nanotube containing a plurality of thymine nucleotides,
a fifth nanotube containing a plurality of uracil nucleotides, and
a sixth nanotube containing a plurality of other nucleotides.

27. The array of claim 22 wherein said substance in each nanotube contains a plurality of an amino acid.

28. The array of claim 22 wherein said substance particles are peptides.

29. The array of claim 22 wherein said substance particles are proteins.

30. The array of claim 22 wherein said substance particles are nucleic acid strands.

31. A method of moving a substance from within a nanotube to an exterior position comprising:
(a) arranging a plurality of particles of said substance in a single-file fashion along the length of said nanotube,
(b) forming at least one nanojump within said nanotube,
wherein said nanojump comprises a localized region within said nanotube wherein the average density of the substance particles within said nanojump differs from the average density of the substance particles in regions of similar size outside of said nanojump but within the same nanotube, and
wherein the substance particles in said regions of similar size outside of said nanojump but within the same nanotube are relatively stationary as substance particles within said nanojump region are transported along said nanotube by said nanojump.

32. The method of claim 31 further comprising depositing said substance onto a substrate.

33. The method of claim 32 wherein said substance is silicon.

34. The method of claim 32 wherein said substance is copper.

35. The method of claim 32 wherein said depositing yields one or more than one quantum dots.

36. The method of claim 32 wherein said substance is gold.

37. The method of claim 32 wherein said substance is gallium.

38. The method of claim 32 wherein said substance is a transition metal.

39. The method of claim 32 wherein said substance is hydrogen.

40. The method of claim 31 further comprising ejecting said substance into a solution.

41. The method of claim 31 wherein said substance is a nucleotide.

42. The method of claim 31 wherein said substance is an amino acid.

43. The method of claim 31 wherein said substance is a peptide.

44. The method of claim 31 wherein said substance is a protein.

45. The method of claim 31 wherein said substance is a nucleic acid strand.

46. The method of claim 31 wherein said substance is silicon.

47. The method of claim 31 wherein said substance is copper.

48. The method of claim 31 wherein said substance is gold.

49. The method of claim 31 wherein said substance is gallium.

50. The method of claim 31 wherein said substance is a transition metal.

51. The method of claim 31 wherein said substance is hydrogen.

52. The method of claim 31 wherein said substance includes nanocrystals.

53. The method of claim 31 wherein said substance includes nanoparticles.

54. The method of claim 31 wherein said quantum dots are formed after said substance is moved from within the nanotube to an exterior position.

55. A method of sequencing a strand of a substance comprising multiple subunits comprising:
moving at least part of a strand of a substance lengthwise through a nanotube by forming at least one nanojump within said nanotube,
wherein said nanojump comprises a localized region within said nanotube wherein the average density of the substance within said nanojump differs from the average density of the substance in regions of similar size outside of said nanojump but within the same nanotube;
and
advancing said substance from within the nanotube by the passage of said at least one nanojump to a location outside of the nanotube by an amount equal to about one single subunit of said substance;
wherein the substance subunits in said regions of similar size outside of said nanojump hut within the same nanotube are relatively stationary as substance subunits within said nanojump region are transported along said nanotube by said nanojump;
and
measuring one or more properties of said one single subunit.

56. The method of claim 55 wherein said substance is a polymer comprising monomer subunits.

57. The method of claim 55 wherein said substance is a protein comprising amino acid subunits.

58. The method of claim 55 wherein said substance is a nucleic acid sequence comprising nucleotide subunits.

59. A method of transporting at least one charged particle through a nanotube comprising:
arranging a chain of substance particles contained within said nanotube in a single file fashion along the length of the nanotube; and
forming at least one nanojump within said nanotube,
wherein said nanojump comprises a localized region within said nanotube wherein the average density of the substance particles within said nanojump differs from the average density of the substance particles in regions of similar size outside of said nanojump but within the same nanotube, and
wherein the substance particles in said regions of similar size outside of said nanojump but within the same nanotube are relatively stationary as substance particles within said nanojump region are transported along said nanotube by said nanojump, and
transporting a charged particle along the chain of substance particles.

60. The method of claim 59 wherein said charged particle is a proton.

61. The method of claim 59 wherein said charged particle is an electron.

62. A system for transporting a substance through a nanotube comprising:
(a) a nanotube having a length and a substance contained within the nanotube, said substance comprising a plurality of molecules arranged in a single-file fashion-along the length of the nanotube, and
(b) a nanojump-forming device coupled to said nanotube, wherein
(1) said nanojump comprises a localized region within said nanotube wherein the average density of the substance particles within said nanojump differs from the average density of the substance particles in regions of similar size outside of said nanojump but within the same nanotube, and
(2) wherein the substance particles in said regions of similar size outside of said nanojump but within the same nanotube are relatively stationary as substance particles within said nanojump region are transported along said nanotube by said at least one nanojump.

63. The system of claim 62 further comprising a detector configured to measure an electric potential difference.

64. A method of generating power comprising:
transporting a substance comprising a plurality of substance particles through a nanotube,
wherein at least a portion of said substance particles couple with at least a or some electrons in the wall of said nanotube yielding an electrical current,
wherein said nanotube has a diameter that is:
(a) larger than the diameter of a single particle of said substance and two atomic radii of the appropriate constituent of the nanotube wall, and
(b) smaller than twice the diameter of a single particle of said substance and two atomic radii of the appropriate constituent of the nanotube wall,
wherein said method further comprises forming at least one nanojump,
wherein said nanojump comprises a localized region within said nanotube wherein the average density of the substance particles within said nanojump differs from the average density of the substance particles in regions of similar size outside of said nanojump but within the same nanotube, and wherein the substance particles in said regions of similar size outside of said nanojump but within the same nanotube are relatively stationary as substance particles within said nanojump region are transported along said nanotube by said at least one nanojump.

65. A method of creating one or more than one nanojump in a nanotube with a substance contained therein, said substance comprising a plurality of particles arranged in a single file fashion along the length of the nanotube, by applying a periodic field to said substance, wherein said nanojump comprises a localized region within said nanotube wherein the average density of the substance particles within said nanojump differs from the average density of the substance particles in regions of similar size outside of said nanojump but within the same nanotube, and wherein the substance particles in said regions of similar size outside of said nanojump but within the same nanotube are relatively stationary as substance particles within said nanojump region are transported along said nanotube by said at least one nanojump.

66. A method of transporting a substance in a nanotube comprising:

forming at least one nanojump in a nanotube comprising a substance, said substance comprising a plurality of substance particles arranged in a single file fashion along the length of the nanotube; and transporting said substance by the passage of at least one nanojump, wherein said nanojump comprises a localized region within said nanotube wherein the average, density of the substance particles within said nanojump differs from the average density of the substance particles in regions of similar size outside of said nanojump but within the same nanotube, and wherein the substance particles within said regions of similar size outside of said nanojump but within the same nanotube remain relatives stationary as substance particles within said nanojump region are transported along said nanotube by said at least one nanojump.

67. The method of claim 66 wherein said substance is a plurality of water molecules arranged in a single-file fashion along the length of the nanotube.

68. The method or claim 67 wherein the temperature of said plurality of water molecules is about 273 K or below.

69. The method of claim 66 wherein said substance is at least one protein oriented lengthwise along the length of the nanotube.

70. The method of claim 66 wherein said substance is at least one nucleic acid strand oriented lengthwise along the length of the nanotube.

71. The method of claim 66 wherein said substance comprises a plurality of amino acids arranged in a single-file fashion along the length of the nanotube.

72. The method of claim 66 wherein said substance comprises a plurality of nucleotides arranged in a single-file fashion along the length of the nanotube.

73. The method of claim 66 wherein the temperature of said substance in said nanotube is below the bulk freezing temperature of said substance under standard pressure.

74. The method of claim 66 wherein the temperature of said substance in said nanotube is about 75 K or below.

75. The method of claim 66 wherein at least one nanojump is formed by application of pressure to the nanotube.

76. The method of claim 66 wherein at least one nanojump is formed by application of an electric field to the nanotube.

77. The method of claim 66 wherein said nanotube has an internal diameter that is between about 5.4 angstroms and about 10.2 angstroms.

78. The method of claim 66 wherein said nanotube has a first end in fluid communication with a first reservoir comprising said substance, wherein said nanotube has a second end in fluid communication with a second reservoir consisting essentially of said substance, and wherein at least some substance is transported from said first reservoir through said nanotube and into said second reservoir.

79. The method of claim 78 wherein said substance is water.

80. The method of claim 66 wherein at least 10 nanojumps are formed.

81. The method of claim 66 wherein the nanotube has a length and a potential difference is applied across the length of the nanotube.

82. The method of claim 66 consisting of 1 or 2 nanojumps.

83. The method of claim 66 further comprising a method of designing said nanotube comprising selecting a number of nanojumps for said nanotube and further comprising three or more of:

(a) selecting a material for nanotube construction;
(b) selecting a substance to be placed within said nanotube;
(c) sizing the nanotube radius to accommodate only a single-file chain of said second substance within the interior of said nanotube; and
(d) sizing the nanotube length to accommodate at least one nanojump.

84. The method of claim 66 further comprising a method of selecting operating conditions for said nanotube comprising at least two of:

(a) selecting a number of nanojumps within said nanotube via external conditions, said number equal to or greater than one;
(b) selecting the distance between nanojumps when more than one nanojump is present;
(c) selecting a type of and magnitude of potential difference to apply across said nanotube; and
(d) selecting a temperature so as to increase transport rates.

85. The method of claim 84 comprising employing the FK model.

86. The method of claim 85 further comprising determining nanojump speed.

87. The method of claim 85 employing the Toda potential.

88. The method of claim 85 employing the Hull function approach.

89. The method of claim 66 further comprising simulating said nanojump computationally using molecular dynamics.

90. The method of claim 89 wherein the temperature of the substance is below the bulk freezing temperature of said substance.

91. The method of claim 89 wherein atoms comprising said nanotube are replaced by a potential energy grid.

92. The method of claim 91 wherein cutoff distances are set larger than about 1.7 nm.

93. The method of claim 89 wherein cutoff distances are set larger than about 1.7 nm and wherein long range electrostatic calculations are turned off.

94. A method of controlling a chemical reaction comprising:
- filling a first nanotube with a substance comprising a plurality of substance particles arranged in a single file fashion along the length of said first nanotube,
- forming at least one nanojump within said first nanotube, wherein said nanojump comprises a localized region within said first nanotube wherein the average density of the substance particles within said nanojump differs from the average density of the substance particles in regions of similar size outside of said nanojump but within said first nanotube; and
    wherein the substance particles within said regions of similar size outside of said nanojump but within the first nanotube remain relatively stationary as substance particles within said nanojump region are transported along said first nanotube by said at least one nanojump;
- forming a second nanotube containing a substance comprising a plurality of substance particles arranged in a single file fashion along the length of said second nanotube,
- forming at least one nanojump within said second nanotube, wherein said nanojump comprises a localized region within said second nanotube wherein the average density of the substance particles within said nanojump differs from the average density of the substance particles in regions of similar size outside of said nanojump but within the second nanotube; and
    wherein the substance particles within said regions of similar size outside of said nanojump but within the second nanotube remain relatively stationary as substance particles within said nanojump region are transported along said second nanotube by said at least one nanojump;
- transporting a least a portion of said first substance from within the first nanotube by the passage of said at least one nanojump to a location outside of the first nanotube; and
- transporting at least a portion of said second substance from within the second nanotube by the passage of said at least one nanojump to a location outside of the second nanotube
- to facilitate a reaction at a location outside of said first nanotube and at a location outside of said second nanotube between at least a portion of said first substance and at least a portion of said second substance.

* * * * *